(12) United States Patent
Gargus et al.

(10) Patent No.: US 7,022,480 B1
(45) Date of Patent: Apr. 4, 2006

(54) EXONS OF THE HSKCA3/KCNN3 GENE

(75) Inventors: J. Jay Gargus, Irvine, CA (US); K. George Chandy, Laguna Beach, CA (US); Vikram Shakkottai, Irvine, CA (US); Hiroaki Tomita, Irvine, CA (US)

(73) Assignee: The Regents of the University of California, Oakland, CA (US)

( * ) Notice: Subject to any disclaimer, the term of this patent is extended or adjusted under 35 U.S.C. 154(b) by 448 days.

(21) Appl. No.: 10/269,503

(22) Filed: Oct. 11, 2002

Related U.S. Application Data

(60) Provisional application No. 60/328,891, filed on Oct. 11, 2001.

(51) Int. Cl.
  *C12Q 1/68* (2006.01)
  *C12N 15/867* (2006.01)
  *C12N 5/02* (2006.01)

(52) U.S. Cl. .................. 435/6; 435/320.1; 435/325

(58) Field of Classification Search ............. 435/6, 435/69.1, 325, 320.1; 530/350
See application file for complete search history.

(56) References Cited

U.S. PATENT DOCUMENTS 5,869,509 A    2/1999  Romine et al.
6,165,719 A   12/2000  Chandy et al.

FOREIGN PATENT DOCUMENTS

| EP | 0563001 B1 | | 2/1996 |
| WO | WO85/01289 | | 3/1985 |
| WO | WO 98/11139 | * | 3/1998 |
| WO | WO00/34248 | | 6/2000 |

OTHER PUBLICATIONS

Phillips, A., J Pharm Pharmacology 53: 1169-1174, 2001.*
Campbell et al. Theriogenology 47(1): 63-72, 1997.*
Wigley et al., Reprod Fert Dev 6: 585-588, 1994.*
Wang et al., Nuc. Acids Res. 27: 4609-4618, 1999.*
Kaufman et al., Blood 94: 3178-3184, 1999.*
Joiner, W.J., et al., "hSK4, a Member of a Novel Subfamily of Calcium-Activated Potassium Channels," *Proc. Natl. Acad. Sci.*, vol. 94, Sep. 1997, pp. 11013-11018.
Köhler, M, et al., "Small-Conductance, Calcium-Activated Potassium Channels from Mammalian Brian," *Science*, vol. 273, Sep. 20, 1996, pp. 1709-1714.
Ghanshani, S., et al., "Up-regulation of the IKCa1 Potassium Channel During T-cell Activation," *The Journal of Biological Chemistry*, vol. 275, No. 47, Nov. 24, 2000, pp. 37137-37149.
Sun, G., et al., "Genomic Organization and Promoter Analysis of Human KCNN3 Gene," *J. Hum. Genet*, vol. 46, 2001, pp. 463-470.
Chandy, K.G., et al., "Isolation of a Novel Potassium Channel Gene hSKCa3 containing a Polymorphic CAG Repeat: A Candidate for Schizophrenia and Bipolar Disorder?," *Molecular Psychiatry*, vol. 3, 1998, pp. 32-37.
Cardno, A.G., et al., "CAG Repeat Length in the hKCa3 Gene and Symptom Dimensions in Schizophrenia," *Society of Biological Psychiatry*, 1999, pp. 1592-1596.
Dror, V., et al., "hKCa3/KCNN3 Potassium Channel Gene: Association of Longer CAG Repeats with Schizophrenia in Israeli Ashkenazi Jews, expression in human tissues and localization to chromosome 1q21," *Molecular Psychiatry*, vol. 4, 1999, pp. 254-260.
Wolfart, J., et al., "Differential Expression of the Small-Conductance, Calcium-Activated Potassium Channel SK3 is Critical for Pacemaker Control in Dopaminergic Midbrain Neurons," The Journal of Neuroscience, vol. 21, No. 10, May 15, 2001, pp. 3443-3456.

(Continued)

*Primary Examiner*—Janet L. Andres
*Assistant Examiner*—Gyan Chandra
(74) *Attorney, Agent, or Firm*—DLA Piper Rudnick Gray Cary US LLP

(57) ABSTRACT

The present invention is based on the discovery and cloning of two variants of the small conductance calcium activated potassium channel type 3 (hKCa3/KCNN3) gene. The isoform variants are identical to the structure of the SKCa3-1a transcript with regard to exons 2–8, but differ in that one variant, SKCa3-1b, contains exon 1b in place of exon 1a and in that the other variant, SKCa3-1c, contains exon 1c in place of exon 1a. When expressed simultaneously with SKCa3-1a, the variants will independently dominantly negatively suppress SKCa3-1a and other functional members of the $SK_{Ca}$ channel family. Accordingly, the present invention provides the novel gene variants, methods for the detection of the variants and treatment of disorders related to the activity of these variants. Kits employing the methods of the invention are also described.

14 Claims, 12 Drawing Sheets

OTHER PUBLICATIONS

Farde, Lars, "Brain Imaging of Schizophrenia-the Dopamine Hypothesis," *Schizophrenia Research*, vol. 28, 1997, pp. 157-162.

Shepard and Bunney, "Effects of Apamin on the Discharge Properties of Putative Dopamine-Containing Neurons in Vitro," *Brain Research*, vol. 463, 1988, pp. 380-384.

Ping and Shepard, Apamin-Sensitive $Ca^{2+}$-Activated $K^+$ Channels Regulate Pacemaker Activity in Nigral Dopamine Neurons, NeuroReport 7, 1996, pp. 809-814.

Ping and Shepard, "Blockage of SK-Type $CA^{2+}$-Activated $K^+$ Channels Uncovers a $CA^{2+}$-Dependent Slow Afterdepolarization in Nigral Dopamine Neurons," *The American Physiological Society*, 1999, pp. 977-984.

Bowen et al., "Mutation Screening of the KCNN3 Gene Reveals a Rare Frameshift Mutation,", *Molecular Psychiatry*, May 6, 2001 (3) pp. 259-260.

Miller, M. J., et al., "Nuclear Localization and Dominant-Negative Suppression by a Mutant SKCa3 N-terminal Channel Fragment Identified in a Patient with Schizophrenia," *The Journal of Biological Chemistry*, vol. 276, No. 30, Jul. 27, 2001, pp. 27753-27756.

Shakkottai, V.G., et al., "Design and Characterization of a Highly Selective Peptide Inhibitor of the Small Conductance Calcium-activated $K^+$ Channel, SkCa2*," *The Journal of Biological Chemistry*, vol. 276, No. 46, Nov. 16, 2001, pp. 43145-43151.

Syme, C.A., et al., "Pharmacological Activation of Cloned Intermediate and Small-Conductance $Ca^{2+}$-Activated $K^+$ Channels," *Am. J. Physiol. Cell Physiol.* vol. 278, 2000, pp. C570-C581.

Cao, Y, et al., "Modulation of Recombinant Small-Conductance $Ca^{2+}$-Activated $K^+$ Channels by the Muscle Relaxant Chlorzoxazone and Structurally Related Compounds," *The Journal of Pharmacology and Experimental Therapeutics*, vol. 296, No. 3, 2001, pp. 683-689.

Matthews, R.T., et al, "Effects of Zoxazolamine and Related Centrally Acting Muscle Relaxants on Nigrostriatal Dopaminergic Neurons," *Brain Research Bulletin*, vol. 12, 1984, pp. 479-486.

McMillen, B.A., et al., "On Central Muscle Relaxants, Strychnine-Insensitive Glycine Receptors and Two Old Drugs; Zoxazolamine and HA-966", J. Neural Transm. Gen. Sect., vol. 89, 1992, pp. 11-25.

* cited by examiner

Figure 1: Comparison of SKCa3-1a, SKCa3-1b and SKCa3-1c
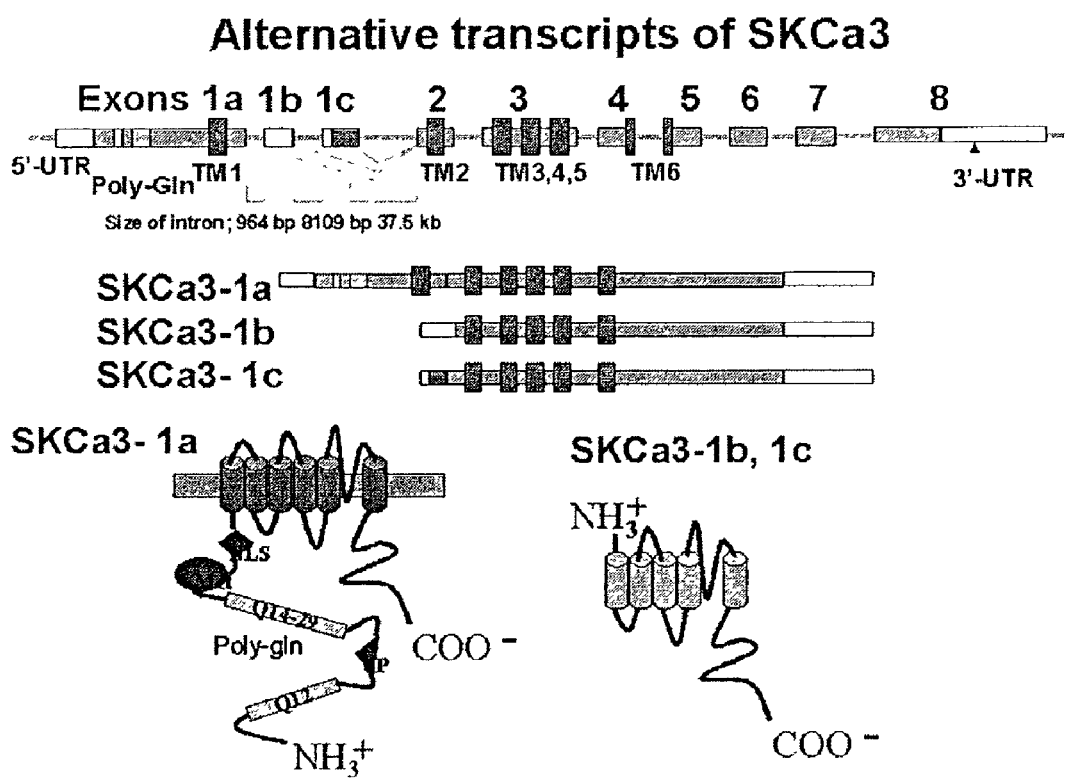

Figure 2: Nucleic acid structure of SKCa3-1b exon 1B

GATGGAGAACAGCAGGCACTGGCTTTAGCGGGGAGCTGGCCCCACTGCTCCAGCCT
CTCAGTCCAGCCCCAAGACGGAGGAGGGGGTTTCCCTCCCAGAGGGAGTGGAGAT
GGAGGAAG (SEQ ID NO: 1; Genbank #AY138901)

1B full length transcript

GATGGAGAACAGCAGGCACTGGCTTTAGCGGGGAGCTGGCCCCACTGCTCCAGCCT
CTCAGTCCAGCCCCAAGACGGAGGAGGGGGTTTCCCTCCCAGAGGGAGTGGAGAT
GGAGGAAGGACTCCATGTTTTCGTTGGCCCTGAAATGCCTTATCAGTCTGTCCACCA
TCATCCTTTTGGGCTTGATCATCGCCTACCACACACGTGAAGTCCAGCTCTTCGTGAT
CGACAACGGCGCGGATGACTGGCGGATAGCCATGACCTACGAGCGCATCCTGTACA
TCAGCCTGGAGATGCTGGTGTGCGCCATCCACCCCATTCCTGGCGAGTACAAGTTCT
TCTGGACGGCACGCCTGGCCTTCTCCTACACACCCTCCCGGGCGGAGGCCGATGTG
GACATCATCCTGTCTATCCCCATGTTCCTGCGCCTGTACCTGATCGCCCGAGTCATG
CTGCTGCACAGCAAGCTCTTCACCGATGCCTCGTCCCGCAGCATCGGGGCCCTCAA
CAAGATCAACTTCAACACCCGCTTTGTCATGAAGACGCTCATGACCATCTGCCCTGG
CACTGTGCTGCTCGTGTTCAGCATCTCTCTGTGGATCATTGCTGCCTGGACCGTCCG
TGTCTGTGAAAGGTACCATGACCAGCAGGACGTAACTAGTAACTTTCTGGGTGCCAT
GTGGCTCATCTCCATCACATTCCTTTCCATTGGTTATGGGGACATGGTGCCCCACAC
ATACTGTGGGAAAGGTGTCTGTCTCCTCACTGGCATCATGGGTGCAGGCTGCACTGC
CCTTGTGGTGGCCGTGGTGGCCCGAAAGCTGGAACTCACCAAAGCGGAGAAGCACG
TTCATAACTTCATGATGGACACTCAGCTCACCAAGCGGATCAAGAATGCTGCAGCCA
ATGTCCTTCGGGAAACATGGTTAATCTATAAACACACAAAGCTGCTAAAGAAGATTGA
CCATGCCAAAGTGAGGAAACACCAGAGGAAGTTCCTCCAAGCTATCCACCAGTTGAG
GAGCGTCAAGATGGAACAGAGGAAGCTGAGTGACCAAGCCAACACTCTGGTGGACC
TTTCCAAGATGCAGAATGTCATGTATGACTTAATCACAGAACTCAATGACCGGAGCGA
AGACCTGGAGAAGCAGATTGGCAGCCTGGAGTCGAAGCTGGAGCATCTCACCGCCA
GCTTCAACTCCCTGCCGCTGCTCATCGCCGACACCCTGCGCCAGCAGCAGCAGCAG
CTCCTGTCTGCCATCATCGAGGCCCGGGGTGTCAGCGTGGCAGTGGGCACCACCCA
CACCCCAATCTCCGATAGCCCCATTGGGGTCAGCTCCACCTCCTTCCCGACCCCGTA
CACAAGTTCAAGCAGTTGCTAAATAAATCTCCCCACTCCAGAAGCATTACCCATAGGT
CTTAAGATGCAAATCAACTCTCTCCTGGTCGCTTTGCCATCAAGAAACATTCAGACCA
GGGAACGGAAAGAAGAGAGACCGAGCTAATTAACTAACTCATGTTCATTCAGCGTGC
TTGGTCCGACATGCCTTGAAACCAGAAATCTAATCTCTGTTTAGGTGCCTCTACTTGG
GAGCGGGAAGAGGAGATGACAGGAAGCGACGCCTCTGGCAGGGCCCTTGCTGCAG
AGTTGGTGGAGAACAGAAATCCACGCTCAATCTCAGGTCTTCACGCGGGGGGTGGG
GGTCAGATGCACTGAAGTAGCCAACAGCGAAACCAGTCCAGAAGAGGGGTCCGCTG
GGAGGGAGGGTTGTGTCAGGCTTGGGGGATGGGCTCTTCGCCATGGGGGTCTTTGA
ACACACCTCTCTCCTTTCCTTTTGTCTACGGAAGCCTCTGGGTGACAAAAGTAAAGA
GAGCTGCCCACAACTTGCCAAAACAGATATACTCGAATCAGACTGAAAAAAAAAAAAA
AAA (SEQ ID NO: 2; Genbank # AY138900)

Figure 3: Nucleic acid structure of SKCa3-1c

1C exon

GAAAGTCAGCTTAAAGGACACTCCTTACAGGGACTGAGCTGGCACCTACTCCTTAGA
GCTTGCTGATACCAGGCCTGCCACGCGACATCTGCAAGGACAGTTGTTTGGTGTTTT
GCTTCAGGTTATAGATGGAGAGACCTATAAAG (SEQ ID NO: 3; Genbank #AF438202)

1C full length transcript

GAAAGTCAGCTTAAAGGACACTCCTTACAGGGACTGAGCTGGCACCTACTCCTTAGA
GCTTGCTGATACCAGGCCTGCCACGCGACATCTGCAAGGACAGTTGTTTGGTGTTTT
GCTTCAGGTTATAGATGGAGAGACCTATAAAGGACTCCATGTTTTCGTTGGCCCTGAA
ATGCCTTATCAGTCTGTCCACCATCATCCTTTTGGGCTTGATCATCGCCTACCACACA
CGTGAAGTCCAGCTCTTCGTGATCGACAACGGCGCGGATGACTGGCGGATAGCCAT
GACCTACGAGCGCATCCTGTACATCAGCCTGGAGATGCTGGTGTGCGCCATCCACC
CCATTCCTGGCGAGTACAAGTTCTTCTGGACGGCACGCCTGGCCTTCTCCTACACAC
CCTCCCGGGCGGAGGCCGATGTGGACATCATCCTGTCTATCCCCATGTTCCTGCGC
CTGTACCTGATCGCCCGAGTCATGCTGCTGCACAGCAAGCTCTTCACCGATGCCTCG
TCCCGCAGCATCGGGGCCCTCAACAAGATCAACTTCAACACCCGCTTTGTCATGAAG
ACGCTCATGACCATCTGCCCTGGCACTGTGCTGCTCGTGTTCAGCATCTCTCTGTGG
ATCATTGCTGCCTGGACCGTCCGTGTCTGTGAAAGGTACCATGACCAGCAGGACGTA
ACTAGTAACTTTCTGGGTGCCATGTGGCTCATCTCCATCACATTCCTTTCCATTGGTT
ATGGGGACATGGTGCCCCACACATACTGTGGGAAAGGTGTCTGTCTCCTCACTGGCA
TCATGGGTGCAGGCTGCACTGCCCTTGTGGTGGCCGTGGTGGCCCGAAAGCTGGAA
CTCACCAAAGCGGAGAAGCACGTTCATAACTTCATGATGGACACTCAGCTCACCAAG
CGGATCAAGAATGCTGCAGCCAATGTCCTTCGGGAAACATGGTTAATCTATAAACACA
CAAAGCTGCTAAAGAAGATTGACCATGCCAAAGTGAGGAAACACCAGAGGAAGTTCC
TCCAAGCTATCCACCAGTTGAGGAGCGTCAAGATGGAACAGAGGAAGCTGAGTGAC
CAAGCCAACACTCTGGTGGACCTTTCCAAGATGCAGAATGTCATGTATGACTTAATCA
CAGAACTCAATGACCGGAGCGAAGACCTGGAGAAGCAGATTGGCAGCCTGGAGTCG
AAGCTGGAGCATCTCACCGCCAGCTTCAACTCCCTGCCGCTGCTCATCGCCGACAC
CCTGCGCCAGCAGCAGCAGCAGCTCCTGTCTGCCATCATCGAGGCCCGGGGTGTCA
GCGTGGCAGTGGGCACCACCCACACCCCAATCTCCGATAGCCCCATTGGGGTCAGC
TCCACCTCCTTCCCGACCCCGTACACAAGTTCAAGCAGTTGCTAAATAAATCTCCCCA
CTCCAGAAGCATTACCCATAGGTCTTAAGATGCAAATCAACTCTCCTGGTCGCTTT
GCCATCAAGAAACATTCAGACCAGGGAACGGAAAGAAGAGAGACCGAGCTAATTAAC
TAACTCATGTTCATTCAGCGTGCTTGGTCCGACATGCCTTGAAACCAGAAATCTAATC
TCTGTTTAGGTGCCTCTACTTGGGAGCGGGAAGAGGAGATGACAGGAAGCGACGCC
TCTGGCAGGGCCCTTGCTGCAGAGTTGGTGGAGAACAGAAATCCACGCTCAATCTCA
GGTCTTCACGCGGGGGGTGGGGGTCAGATGCACTGAAGTAGCCAACAGCGAAACCA
GTCCAGAAGAGGGGTCCGCTGGGAGGGAGGGTTGTGTCAGGCTTGGGGGATGGGC
TCTTCGCCATGGGGGTCTTTGAACACACCTCTCTCCTTTCCTTTTGTCTACGGAAGCC
TCTGGGTGACAAAAGTAAAAGAGAGCTGCCCACAACTTGCCAAAACAGATATACTCG
AATCAGACTGAAAAAAAAAAAAAAAAA (SEQ ID NO: 4; Genbank #AF438203)

Figure 4:

*Distribution of SKCa3-1A and SK3-1B mRNA in human tissues determined by Taqman™ quantitative RT-PCR.* (A-C) Pooled human tissues. (D-F) brain regions from a single donor. SKCa3-1A (A, D) and SKCa3-1B (B, E) mRNA copy number per µl cDNA expressed as mean ± SD. (C, F) SKCa3-1B/SKCa3-1A ratio displayed as a percentage. The horizontal lines in Figs. A and B show the arbitrary division into abundant, intermediate and low expression levels. * No detectable transcript.

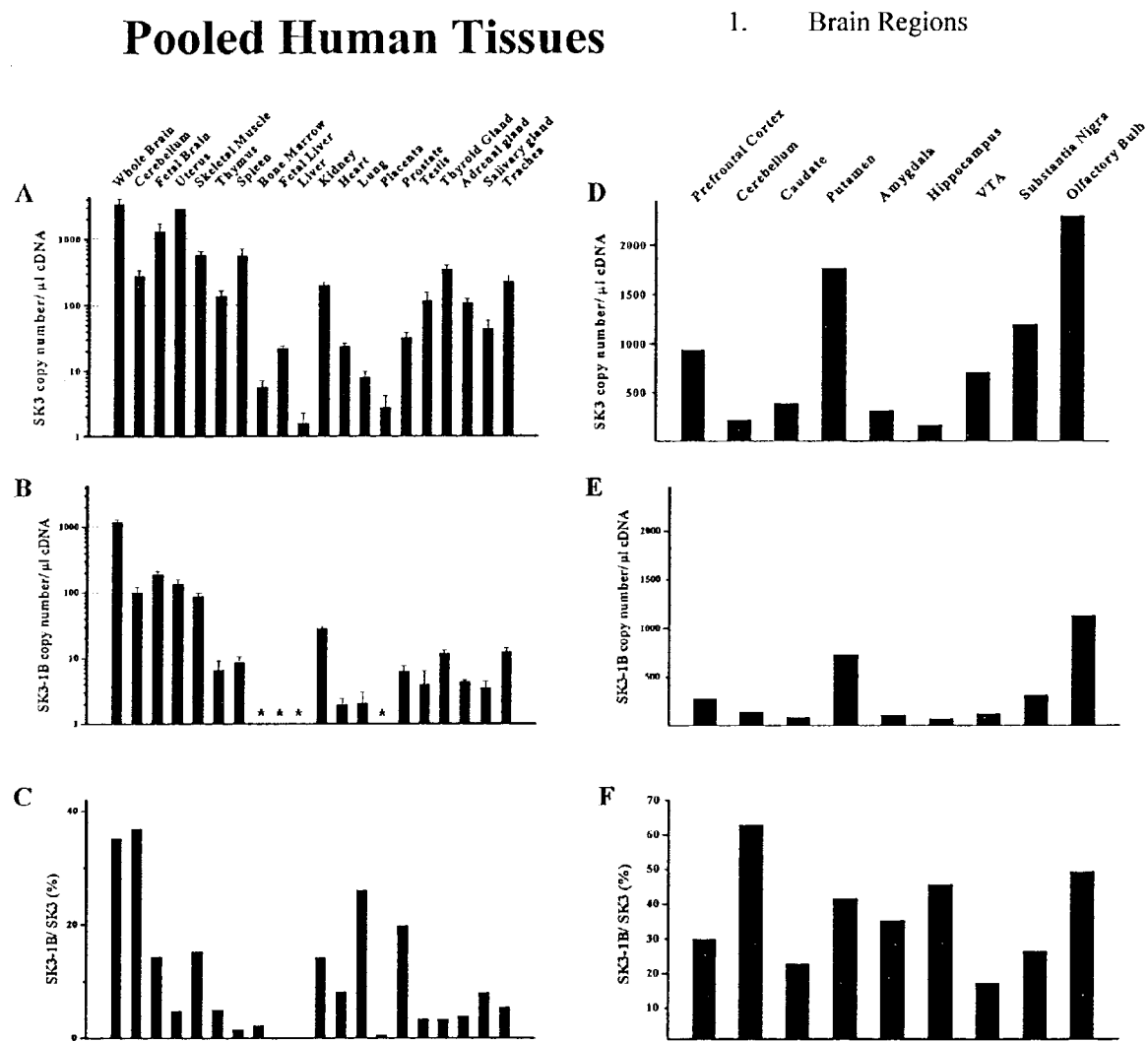

Figure 5A: Currents produced by SKCa3-1A
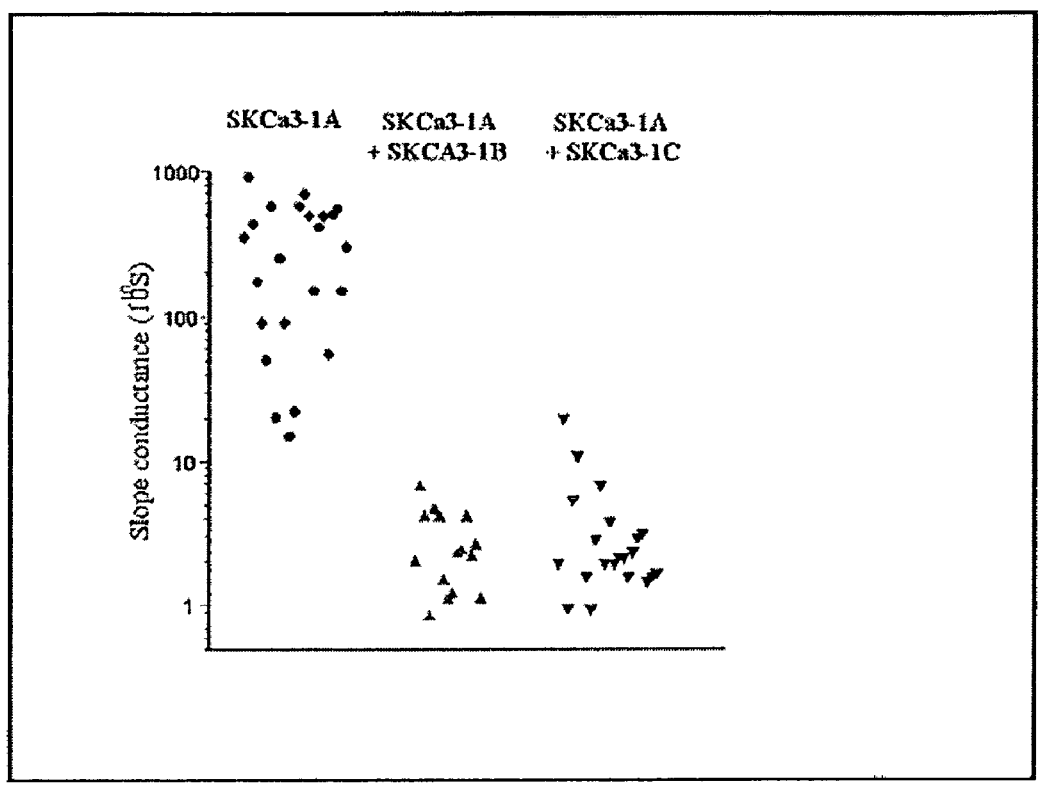

Figure 5B:

*Scatter plot showing the effect of SKCa3-1B-GFP and SKCa3-1B-IRES-GFP on endogenous SKCa3-1A and $K_V$ currents in PC12 cells.* SKCa3-1A currents (mean ± SEM) in untransfected (open squares; 6.24  1.57 nS, n = 22), SKCa3-1B-GFP-transfected (open triangles, 0.68  0.08 nS, n = 11; p = 0.018) and SKCa3-1B-IRES-GFP-transfected PC12 cells (open circles; 1.1  .03 nS, n = 12; p = 0.024). $K_V$ currents (mean ± SEM) in untransfected (filled squares; 707.94  147.7 pA, n = 15), SKCa3-1B-GFP-transfected (filled triangles; 475.96  61.78 pA, n = 15; p > 0.05) and SKCa3-1B-IRES-GFP-transfected PC12 cells (filled circles; 560.37  75.9 pA, n = 14; p > 0.05). The data was analyzed by a Student t-Test between the respective transfected cell population and the untransfected PC12 cells.

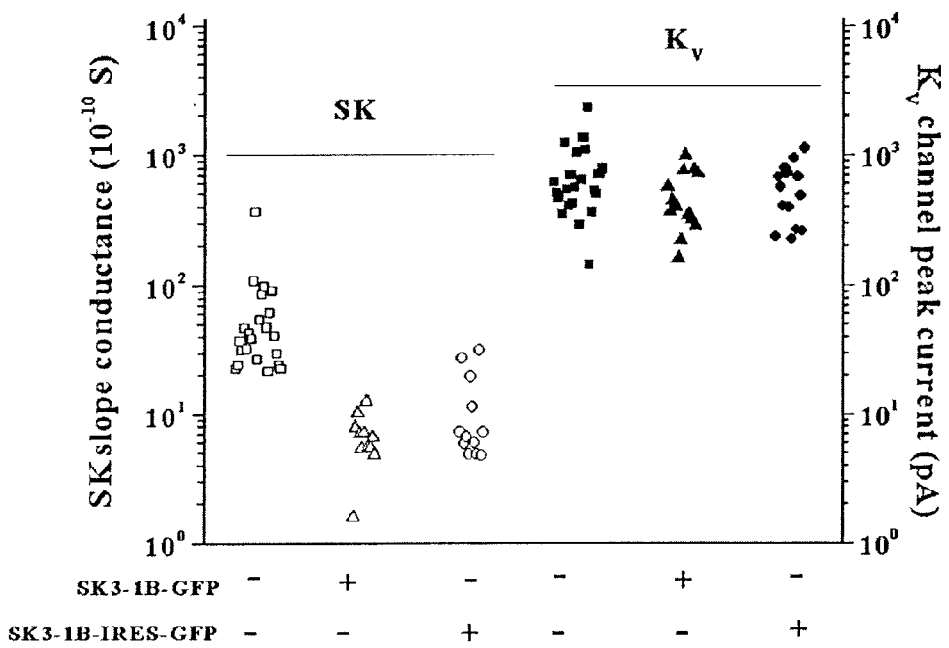

A

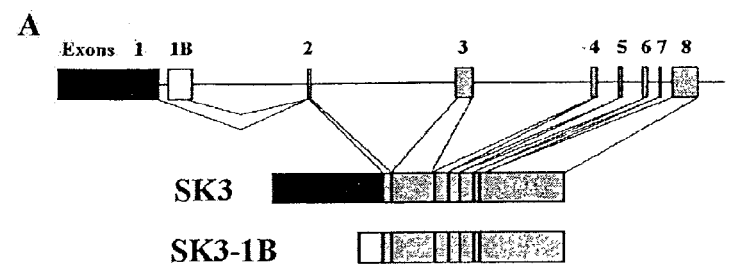

B

| | EXON-1 | | EXON-2 |
|---|---|---|---|
| SK3 gen | TACTCAAAGgtaggg | 46839 bp | tcctgcagGACTCCATGTTTTCGTTGGCCCTGAAATGCCTT |
| SK3 cDNA | TACTCAAAG | | GACTCCATGTTTTCGTTGGCCCTGAAATGCCTT |
| SK3 PROT | TyrSerLys | | AspSerMetPheSerLeuAlaLeuLysCysLeu |

| | EXON-1 B | | EXON-2 |
|---|---|---|---|
| SK3-1B gen | TGGAGGAAGgtgggt | 45756 bp | tcctgcagGACTCCATGTTTTCGTTGGCCCTGAAATGCCTT |
| SK3-1B cDNA | TGGAGGAAG | | GACTCCATGTTTTCGTTGGCCCTGAAATGCCTT |
| SK3-1B PROT | | | MetPheSerLeuAlaLeuLysCysLeu |

C

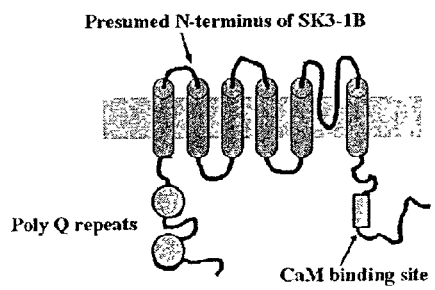

FIGURE 7

SEQUENCE LISTING

<160> NUMBER OF SEQ ID NOS: 13

<210> SEQ ID NO 1
<211> LENGTH: 119
<212> TYPE: DNA
<213> ORGANISM: Homo sapiens

<400> SEQUENCE: 1

```
gatggagaac agcaggcact ggctttagcg gggagctggc cccactgctc cagcctctca    60
gtccagcccc aagacggagg aggggtttc cctcccagag ggagtggaga tggaggaag     119
```

<210> SEQ ID NO 2
<211> LENGTH: 1933
<212> TYPE: DNA
<213> ORGANISM: Homo sapiens

<400> SEQUENCE: 2

```
gatggagaac agcaggcact ggctttagcg gggagctggc cccactgctc cagcctctca    60
gtccagcccc aagacggagg aggggtttc cctcccagag ggagtggaga tggaggaagg    120
actccatgtt ttcgttggcc ctgaaatgcc ttatcagtct gtccaccatc atccttttgg    180
gcttgatcat cgcctaccac acacgtgaag tccagctctt cgtgatcgac aacggcgcgg    240
atgactggcg gatagccatg acctacgagc gcatcctgta catcagcctg agatgctgg    300
tgtgcgccat ccaccccatt cctggcgagt acaagttctt ctggacggca cgcctggcct    360
tctcctacac accctcccgg gcggaggccg atgtggacat catcctgtct atccccatgt    420
tcctgcgcct gtacctgatc gcccgagtca tgctgctgca cagcaagctc ttcaccgatg    480
cctcgtcccg cagcatcggg gccctcaaca agatcaactt caacacccgc tttgtcatga    540
agacgctcat gaccatctgc cctggcactg tgctgctcgt gttcagcatc tctctgtgga    600
tcattgctgc ctggaccgtc cgtgtctgtg aaaggtacca tgaccagcag gacgtaacta    660
gtaactttct gggtgccatg tggctcatct ccatcacatt cctttccatt ggttatgggg    720
acatggtgcc ccacacatac tgtgggaaag gtgtctgtct cctcactggc atcatgggtg    780
caggctgcac tgcccttgtg gtggccgtgg tgcccgaaa gctggaactc accaaagcgg    840
agaagcacgt tcataacttc atgatggaca ctcagctcac caagcggatc aagaatgctg    900
cagccaatgt ccttcgggaa acatggttaa tctataaaca cacaaagctg ctaaagaaga    960
ttgaccatgc caaagtgagg aaacaccaga ggaagttcct ccaagctatc caccagttga   1020
ggagcgtcaa gatggaacag aggaagctga gtgaccaagc caacactctg gtggacctttt   1080
ccaagatgca gaatgtcatg tatgacttaa tcacagaact caatgaccgg agcgaagacc   1140
tggagaagca gattggcagc ctggagtcga agctggagca tctcaccgcc agcttcaact   1200
ccctgccgct gctcatcgcc gacacccctgc gccagcagca gcagcagctc ctgtctgcca   1260
tcatcgaggc ccggggtgtc agcgtggcag tgggcaccac ccacacccca atctccgata   1320
gccccattgg ggtcagctcc acctccttcc cgaccccgta cacaagttca gcagttgct   1380
aaataaatct ccccactcca gaagcattac ccataggtct taagatgcaa atcaactctc   1440
```

-continued

| | |
|---|---|
| tcctggtcgc tttgccatca agaaacattc agaccaggga acggaaagaa gagagaccga | 1500 |
| gctaattaac taactcatgt tcattcagcg tgcttggtcc gacatgcctt gaaaccagaa | 1560 |
| atctaatctc tgtttaggtg cctctacttg ggagcgggaa gaggagatga caggaagcga | 1620 |
| cgcctctggc agggcccttg ctgcagagtt ggtggagaac agaaatccac gctcaatctc | 1680 |
| aggtcttcac gcggggggtg ggggtcagat gcactgaagt agccaacagc gaaaccagtc | 1740 |
| cagaagaggg gtccgctggg agggagggtt gtgtcaggct gggggatgg gctcttcgcc | 1800 |
| atggggtct ttgaacacac ctctctcctt tccttttgtc tacggaagcc tctgggtgac | 1860 |
| aaaagtaaaa gagagctgcc cacaacttgc caaaacagat atactcgaat cagactgaaa | 1920 |
| aaaaaaaaaa aaa | 1933 |

<210> SEQ ID NO 3
<211> LENGTH: 146
<212> TYPE: DNA
<213> ORGANISM: Homo sapiens

<400> SEQUENCE: 3

| | |
|---|---|
| gaaagtcagc ttaaaggaca ctccttacag ggactgagct ggcacctact ccttagagct | 60 |
| tgctgatacc aggcctgcca cgcgacatct gcaaggacag ttgtttggtg ttttgcttca | 120 |
| ggttatagat ggagagacct ataaag | 146 |

<210> SEQ ID NO 4
<211> LENGTH: 1960
<212> TYPE: DNA
<213> ORGANISM: Homo sapiens

<400> SEQUENCE: 4

| | |
|---|---|
| gaaagtcagc ttaaaggaca ctccttacag ggactgagct ggcacctact ccttagagct | 60 |
| tgctgatacc aggcctgcca cgcgacatct gcaaggacag ttgtttggtg ttttgcttca | 120 |
| ggttatagat ggagagacct ataaaggact ccatgttttc gttggccctg aaatgcctta | 180 |
| tcagtctgtc caccatcatc cttttgggct tgatcatcgc ctaccacaca cgtgaagtcc | 240 |
| agctcttcgt gatcgacaac ggcgcggatg actggcggat agccatgacc tacgagcgca | 300 |
| tcctgtacat cagcctggag atgctggtgt gcgccatcca ccccattcct ggcgagtaca | 360 |
| agttcttctg gacggcacgc ctggccttct cctacacacc ctcccgggcg gaggccgatg | 420 |
| tggacatcat cctgtctatc cccatgttcc tgcgcctgta cctgatcgcc cgagtcatgc | 480 |
| tgctgcacag caagctcttc accgatgcct cgtcccgcag catcggggcc ctcaacaaga | 540 |
| tcaacttcaa caccgcttt gtcatgaaga cgctcatgac catctgccct ggcactgtgc | 600 |
| tgctcgtgtt cagcatctct ctgtggatca ttgctgcctg gaccgtccgt gtctgtgaaa | 660 |
| ggtaccatga ccagcaggac gtaactagta actttctggg tgccatgtgg ctcatctcca | 720 |
| tcacattcct ttccattggt tatgggaca tggtgcccca cacatactgt gggaaaggtg | 780 |
| tctgtctcct cactggcatc atgggtgcag gctgcactgc ccttgtggtg gccgtggtgg | 840 |
| cccgaaagct ggaactcacc aaagcggaga agcacgttca taacttcatg atggacactc | 900 |
| agctcaccaa gcggatcaag aatgctgcag ccaatgtcct tcgggaaaca tggttaatct | 960 |
| ataaacacac aaagctgcta aagaagattg accatgccaa agtgaggaaa caccagagga | 1020 |
| agttcctcca agctatccac cagttgagga gcgtcaagat ggaacagagg aagctgagtg | 1080 |
| accaagccaa cactctggtg gaccttccca gatgcagaa tgtcatgtat gacttaatca | 1140 |
| cagaactcaa tgaccggagc gaagacctgg agaagcagat tggcagcctg gagtcgaagc | 1200 |

```
tggagcatct caccgccagc ttcaactccc tgccgctgct catcgccgac accctgcgcc    1260
agcagcagca gcagctcctg tctgccatca tcgaggcccg gggtgtcagc gtggcagtgg    1320
gcaccaccca caccccaatc tccgatagcc ccattgggt cagctccacc tccttcccga     1380
ccccgtacac aagttcaagc agttgctaaa taaatctccc cactccagaa gcattaccca    1440
taggtcttaa gatgcaaatc aactctctcc tggtcgcttt gccatcaaga aacattcaga    1500
ccagggaacg gaaagaagag agaccgagct aattaactaa ctcatgttca ttcagcgtgc    1560
ttggtccgac atgccttgaa accagaaatc taatctctgt ttaggtgcct ctacttggga    1620
gcgggaagag gagatgacag gaagcgacgc ctctggcagg gcccttgctg cagagttggt    1680
ggagaacaga aatccacgct caatctcagg tcttcacgcg gggggtgggg gtcagatgca    1740
ctgaagtagc caacagcgaa accagtccag aagagggtc cgctgggagg gagggttgtg     1800
tcaggcttgg gggatgggct cttcgccatg ggggtctttg aacacacctc tctcctttcc    1860
ttttgtctac ggaagcctct gggtgacaaa agtaaaagag agctgcccac aacttgccaa    1920
aacagatata ctcgaatcag actgaaaaaa aaaaaaaaa                            1960

<210> SEQ ID NO 5
<211> LENGTH: 8
<212> TYPE: DNA
<213> ORGANISM: Homo sapiens
<220> FEATURE:
<221> NAME/KEY: misc_feature
<222> LOCATION: (2)..(3)
<223> OTHER INFORMATION: n is any nucleotide
<220> FEATURE:
<221> NAME/KEY: misc_feature
<222> LOCATION: (5)..(5)
<223> OTHER INFORMATION: n is any nucleotide

<400> SEQUENCE: 5 tnntngyg                                                              8

<210> SEQ ID NO 6
<211> LENGTH: 27
<212> TYPE: DNA
<213> ORGANISM: Artificial sequence
<220> FEATURE:
<223> OTHER INFORMATION: Amplification primer

<400> SEQUENCE: 6
cctccatctc cactccctct gggaggg                                         27

<210> SEQ ID NO 7
<211> LENGTH: 20
<212> TYPE: DNA
<213> ORGANISM: Artificial sequence
<220> FEATURE:
<223> OTHER INFORMATION: Amplification primer

<400> SEQUENCE: 7
cccctcctcc gtcttggggc                                                 20

<210> SEQ ID NO 8
<211> LENGTH: 25
<212> TYPE: DNA
<213> ORGANISM: Artificial sequence
<220> FEATURE:
<223> OTHER INFORMATION: Forward primer

<400> SEQUENCE: 8
```

```
tgttatggtg atagagaccg agctc                                          25

<210> SEQ ID NO 9
<211> LENGTH: 18
<212> TYPE: DNA
<213> ORGANISM: Artificial sequence
<220> FEATURE:
<223> OTHER INFORMATION: Forward primer

<400> SEQUENCE: 9
agccccaaga cggaggag                                                  18

<210> SEQ ID NO 10
<211> LENGTH: 24
<212> TYPE: DNA
<213> ORGANISM: Artificial sequence
<220> FEATURE:
<223> OTHER INFORMATION: Reverse primer

<400> SEQUENCE: 10
tggacagact gataaggcat ttca                                           24

<210> SEQ ID NO 11
<211> LENGTH: 20
<212> TYPE: DNA
<213> ORGANISM: Artificial sequence
<220> FEATURE:
<223> OTHER INFORMATION: Reverse primer

<400> SEQUENCE: 11
ggccaacgaa aacatggagt                                                20

<210> SEQ ID NO 12
<211> LENGTH: 31
<212> TYPE: DNA
<213> ORGANISM: Artificial sequence
<220> FEATURE:
<223> OTHER INFORMATION: Forward primer

<400> SEQUENCE: 12
tgtactcaaa ggactccatg ttttcgttgg c                                   31

<210> SEQ ID NO 13
<211> LENGTH: 25
<212> TYPE: DNA
<213> ORGANISM: Artificial sequence
<220> FEATURE:
<223> OTHER INFORMATION: Reverse primer

<400> SEQUENCE: 13
tcccagaggg agtggagatg gagga                                          25
```

EXONS OF THE HSKCA3/KCNN3 GENE

RELATED APPLICATIONS

This application claims priority under 35 U.S.C. §119(e) from U.S. provisional application Ser. No. 60/328,891, filed Oct. 11, 2001 herein incorporated by reference in its entirety.

GOVERNMENT INTERESTS

This invention was made with Government support under Grant No. RO1 MH59222, awarded by the National Institutes of Health. Accordingly, the U.S. Government may have certain rights in this invention.

BACKGROUND OF THE INVENTION

1. Field of the Invention

This invention relates generally to the field of small conductance calcium activated potassium channels, and more specifically to two variants of the hSKCa3/SK3/KCNN3 gene used in the diagnosis, study, prevention and treatment of disorders related to these channels.

2. Background Information

Action potentials in vertebrate neurons are followed by an after hyperpolarization (AHP) that may persist for several seconds and may have profound consequences for the neuronal firing pattern. The AHP has several components, which are distinct and are mediated by different calcium activated potassium channels. Small conductance calcium activated potassium channels (SKCa, where "S" represents "small") underlie slow components of the AHP, which are responsible for spike-frequency adaption (Hotson, J. R., and Prince, D. A., J. Neurophysiol. 43:409, 1980.).

Small conductance channels have a unitary conductance of 4–14 ps, are exquisitely sensitive to internal $Ca^{2+}$, lack the property of voltage dependence and are blocked by nanomolar concentrations of the natural toxins apamin and scyllatoxin. These channels modulate the firing pattern of neurons via the generation of slow membrane afterhyperpolarizations (Nicoll, R. A., Science 241:545–551, 1988.). As small-conductance calcium-activated $K^+$ channels are responsible for the afterhyperpolarization that follows each action potential in neurons, they thereby modulate neuronal firing frequency. Three phylogenetically related genes, KCNN1/SKCa1/SK1. KCNN2/SKCa2/SK2 and KCNN3/SKCa3/SK3 (Kohler et al., Science 273, 1709–1714, 1996), with a conserved gene structure (Ghanshani et al., J. Biol. Chem. 275, 37137–37149, 2000) encode this family of channels.

The sequence of the functional cDNA that encodes one subunit of the homotetrameric calcium-activated small-conductance $K^+$ channel SKCa3/SK3/KCNN3 is set forth in U.S. Pat. No. 6,165,719. Additionally, the complete 160 kb sequence of the KCNN3 genomic locus has been reported. The sequence has been recorded and assigned accession number AF336797. It is known that within this structure KCNN3 has 8 exons (Sun et al., J. Hum. Genet. 46, 463–470, 2001.).

The $SK_{Ca}$ are currents that have been described in a wide range of tissues, including brain (Lancaster, B. and Nicoll, R. A., J. Physiol. 389:187–203, 1987), peripheral neurons (Goh, J. W., and Pennefather, P. S., J. Physiol. 394:315–330, 1987), skeletal muscle (Romey, G., and Lazdunski, M., Biochem. Biophys. Res. Commun. 118:669–674, 1984) adrenal chromaffin cells (Neely, A., and Lingle, C. J., J. Physiol. 452:97–13 13, 1992), leukocytes (Grissmer, S., et al., J. Gen. Physiol. 99:63–84, 1992), erythrocytes (Hamill, O. P., J. Physiol. 319:97P–98P, 1981), colon (Lomax, R. B., et al., Gut 38:243–247, 1996), and airway epithelia (Welsh, M. J., and McCann, J. D., Proc. Natl. Acad. Sci. USA 82:8823–8826, 1985.). Certain types of $SK_{Ca}$ channels have been distinguished by their sensitivities to the bee venom apamin, whereas other functionally related conductances appear insensitive (Sah, P., and AcLachlan, E. M., 1992, J. Neurophysiol. 74:1772–1776.). The distinguishing features of the $SK_{Ca}$ channels from the maxi-K calcium activated (BK) potassium channels are the $SK_{Ca}$ channels' low conductance (less than 50 pS), the weak or negligible dependence of their activity on membrane voltage, and their high affinity for calcium ($EC_{50}<1$ µM) (e.g., Lancaster, B., and Zucker, R. S., J. Physiol. 475:229–239, 1994.).

Recently, Imbert et al. reported the cloning of six novel cDNAs, each containing one or more long CAG repeats. These cDNAs were isolated from a lymphoblastoid cell cDNA expression library generated from patients with autosomal dominant cerebellar ataxia with a monoclonal antibody specific for polyglutamine sequences (Imbert et al., Nature Genetics 14:285, 1996.). One of the cDNAs, designated AAD14, encoded the partial sequence of a putative protein of 228 amino acids in length. This polypeptide of unknown function contained two long polyglutamine stretches.

Kohler et al. first described a rat small conductance calcium activated potassium channel (rSKCa3) gene, and published the truncated form of the gene (Kohler et al., Science 274:1709, 1996.). An alignment of the known members of the small conductance calcium-activated potassium channels was described by Joiner et al. (Proc. Natl. Acad. Sci. 94: 11013, 1997), who cloned the hSK4 gene, using the potassium channel signature sequence TXX-TXGYG (SEQ ID NO: 5). Ishii et al. (Proc. Natl. Acad. Sci. USA 94:11651–6, 1997) also cloned the intermediate conductance calcium-activated potassium channel h1K1, also known as hSK4.

Schizophrenia is a chronic disabling disorder with a lifetime morbid risk of 1% in the general population. The illness has a significant genetic component (Kendler, K. S., In: Relatives at Risk for Mental Disorders, Dunner, D. L., Gershon, E. S., and Barrett, J. E. (eds.), Raven Press, New York, pp. 247–263, 1988) and often develops in early adulthood. The disease is characterized by a constellation of symptoms including hallucinations and delusions, disordered thinking and concentration, inappropriate emotional responses, catatonia, erratic behavior, and social and occupational deterioration. Although still controversial, "anticipation" (an increase in severity through successive generations) has been found in studies of affected families (Bassett, A. S., and Honer, W. G., Am. J. Hum. Genet., 54:864–870, 1994.). Trinucleotide repeat expansions have been found to underlie several Mendelian hereditary neurological diseases (Ashley, C. T., Jr., and Warren, S. T., Annu. Rev. Genet., 29:703–728, 1995; Timchenko, L. T., and Caskey, C. T., FASEB J., 10:1589–1597, 1996; among others).

Several human hereditary neurological diseases, such as Huntington's disease, fragile X syndrome, myotonic dystrophy, spinal and bulbar muscular atrophy, Machado-Joseph disease, Friedrich's disease and spinocerebellar ataxia, are associated with expanded trinucleotide repeats (typically>35) within the coding region (e.g., Timchenko, L. T., and Caskey, C. T., FASEB J. 10: 1589–97, 1996; Hannan, A. J., J. Clin. Exp. Pharm. Physiol. 23:1015–20, 1996; Bates, G., Bioessays 18:1 75–8, 1996), untranslated sequences (e.g., Warren, S. T., and Ashley, C. T., Ann. Rev. Neurosci.

18:77–99, 1995; Tsilfidis, C., et al, *Nature Genet.* 1:192–195, 1992), or introns (Campuzano, V., et al., *Science* 271:1423–7, 1996) of genes. An association has been shown between the presence of anonymous CAG/CTG repeats and the development of schizophrenia and bipolar disease (O'Donovan, M. C., et al., *Nature Genetics* 10:380–1, 1995; O'Donovan et al., *Psychological Med.* 26:1145–1153, 1996; Cardino, A. G., et al., *Brit. J. Psychiatry* 169:766–771, 1996.).

KCNN3/SK3 has been mapped to chromosome 1q21 (Dror et al., *Mol. Psych.* 4, 254–260, 1999), a region strongly linked to schizophrenia (Brzustowicz et al., *Science* 288, 678–682, 2000) and more recently linked to Finnish Asperger syndrome, thought to be a childhood form of the disease.

KCNN3 contains two polymorphic polyglutamine repeats in the N-terminus. Such long repeats are highly overrepresented in patients with schizophrenia compared to ethnic controls (Chandy et al., *Mol. Psych.* 3, 32–37, 1998; Dror et al., *Mol. Psych.* 4, 254–260, 1999.). Two independent studies have noted a strong association between long repeats and negative-symptom type schizophrenia (Cardno et al., *Biol. Psych.* 45, 1592–1596, 1999; Ritsner M, Modai I, Amir S, Halperin T, Weizman A, et al., An association of CAG repeats at the KCNN3 locus with symptom dimensions of schizophrenia. *Biol Psychiatry,* 2002. 51: 788–794).

Others have not been able to reproduce this association (Antonarakis et al., *Am. J. Med. Genet.* 88, 348–351, 1999, Joober et al, *Am. J. Med. Genet.* 88, 154–157, 1999; Bonner-Brilhault et al., *Eur. J. Hum. Genet.* 7, 247–250, 1999, Hawi et al., *Mol. Psych.* 4, 488–491, 1999; Chowdari et al., *Mol. Psych.* 5, 237–238, 2000.).

Intergenerational lengthening of expanded trinucleotide repeats is thought to underlie the phenomenon of "anticipation" (Ashley and Warren, 1995, supra) observed in schizophrenia and bipolar disease, wherein the disease worsens with subsequent generations (Johnson, J. E., et al., Amer. J. Med. Genet. 75:275–280, 1997; Lipp, O., et al., *Psychiatric Genet.* 5:S8, 1995; Serbanescu-Grigorow, M., et al., *Psychiatric Genet.* 5:S10, 1995.). The subset of these mutations caused by expansions of the CAG trinucleotide have been found only within the coding region of genes, and the encoded polyglutamine arrays may occur in different places within the open-reading-frame (Housman, D., *Nature Genet.* 10:3–4, 1995.). In the past few years, expanded "anonymous" CAG repeats in unidentified genes have been reported in patients with schizophrenia, with considerable overlap between allele distributions in patients and controls (O'Donovan, M. C., et al., *Nature Genet.* 10:380–381, 1995; Morris, A. G., et al., Hum. Mol. Genet., 4:1957–1961, 1995; O'Donovan, M. C., et al., *Psychol. Med.* 26:1145–1153, 1996; O'Donovan, M. C., and Owen, M. J., *Psychol. Med.* 26:1–6, 1996; O'Donovan, M. C., and Owen, M. J., *Annals Med.* 28:541–546, 1996a).

The expression of KCNN3/SKCa3 transcripts in dopaminergic neurons of the human midbrain have been demonstrated using in situ hybridization and quantitative PCR (Dror et al., *Mol. Psych.* 4, 254–260, 1999; Tomita et al, *Mol Psych* In press). Others have demonstrated that KCNN3/SKCa3 is the "pacemaker" that regulates neuronal firing frequency in dopaminergic neurons of the ventral tegmental area (Wolfart et al., *J. Neurosci.* 21, 3443–3456, 2001.).

The syndrome of schizophrenia has been long-associated with over-activity of the dopaminergic pathways (e.g. Farde et al., *Schizophr. Res.* 28, 157–162, 1997.). This finding has been pharmacologically re-confirmed by the fact that drugs currently used to treat the disorder have a clinical potency linearly correlated with their affinity for the dopamine D2 receptor, a receptor most prominently displayed in the VTA and striatum. Apamin, a potent and selective inhibitor of $SK_{Ca}$ channels, is known to block the post-spike afterhyperpolarization and change the firing pattern in dopaminergic neurons from a pacemaker-like discharge into a multiple bursting pattern (Shepard and Bunney *Brain Res.* 463, 380–384, 1988; Ping and Shepard *Neuroreport* 7, 809–814, 1996; Ping and Shepard *J. Neurophysiol.* 81, 977–984, 1999.). Bursting activity in turn has been associated with increased dopamine release (Steketee et al., *J. Pharmacol. Exp Ther.* 254, 711–719, 1990; Manley et al. *J. Neurochem.* 58, 1491–1498, 1992; Morikawa et al., *J. Neurosci.* 20, RC103 1–5, 2000.).

In one study, a 4 base-pair deletion in SKCa3 was reported in a patient with schizophrenia (Bowen et al., *Mol. Psych.* 6, 259–260, 2001), which truncates the protein at the N-terminus (referred to here as SKCa3-1/285). GFP-tagged SKCa3-1/285 localizes rapidly and exclusively to the nucleus of mammalian cells, whereas full-length SKCa3 is excluded from the nucleus and expresses as functional channels (Miller et al., *J. Biol. Chem.* 276, 27753–27756, 2001.). Such neuronal nuclear inclusions have been implicated in apoptosis in other trinucleotide repeat diseases, such as Huntington disease. Postmortem and neuroimaging studies have resulted in observations that there may be an alteration in the neuronal architecture in schizophrenia (Mc-Glashan and Hoffman, *Arch. Gen. Psych.* 57, 637–648, 2000; Halliday, *Clin. Exp. Pharmacol. Physiol.* 28, 64–654, 2001.).

SKCa3-1/285 dominant-negatively suppresses endogenous $SK_{Ca}2$ currents in Jurkat T cells. While the mechanism of suppression remains unknown, it is hypothesized that the suppression occurs via co-assembly into non-functional tetramers (Miller et al., *J. Biol. Chem.* 276, 27753–27756, 2001.). Dominant-negative suppression by SKCa3–1/285 could lead to a global reduction of the entire family of SKCa1–SKCa3 channels in a fashion more potent than traditional allele-specific genetic suppression involving a single locus. Such reduction of all endogenous $SK_{Ca}$ currents, many of them in dopaminergic neurons, might have effects analogous to the $SK_{Ca}$ blocker apamin.

SUMMARY OF THE INVENTION

The present invention relates to the discovery of SKCa3-1b and SKCa3-1c, two novel isoform variants of the SK3 gene. the SK3 gene and its structure are set forth in U.S. Pat. No. 6,165,719. The present invention provides such genes, methods for their detection and treatment of heritable neurological and psychiatric disorders based upon activity of the genes.

In one aspect, the invention is directed to an isolated polynucleotide encoding the SKCa3-1b or SKCa3-1c variants of the SK3 gene. The full-length polynucleotides of the invention are set forth in SEQ ID NO:2 and SEQ ID NO:4, but also include RNA corresponding to those sequences, sequences complementary to those sequences and fragments of any of the above that are at least 15 bases in length and that will selectively hybridize to DNA which encodes a SKCa3-1B or SKCa3-1C protein.

In another aspect, the invention is directed to a method of treating a disorder associated with the dysfunction of the $SK_{Ca}$ channel itself, or of a channel regulated by that channel, by administering an agent that activates the $SK_{Ca}$ channel function, where the disorder results from expression of SKCa3-1b or SKCa3-1c and/or suppression of SKCa3-1a.

In still another aspect, the invention is directed to a method of diagnosing a disorder associated with the dysfunction of the $SK_{Ca}$ channel itself, or of a channel regulated by that channel, by detecting the presence of an abundance of SKCa3-1b or SKCa3-1c in a sample from a patient suspected of having the disorder. The detection of altered abundance of SKCa3-1b or SKCa3-1c is indicative of a disorder associated with $SK_{Ca}$ channel dysfunction.

In yet another aspect, the invention is directed to a kit useful for the detection of a target nucleic acid sequence in a sample from a subject having a disorder associated with dysfunction of the $SK_{Ca}$ channel. The presence of the target nucleic acid sequence in the sample is indicative of having or being predisposed to having a disorder associated with dysfunction of the $SK_{Ca}$ channel. The kit is made up of one or more containers, where a first container contains oligonucleotides which allow amplification of full-length SKCa3-1b or SKCa3-1c such that full-length SKCa3-1b or SKCa3-1c nucleic acid is detected. In the kit, full length SKCa3-1b or SKCa3-1c nucleic acid sequence encodes an amino acid sequence that negative dominantly suppresses $SK_{Ca}$ channel function.

In still another aspect of the invention, the polynucleotides of exons 1b and 1c, which distinguish the full length sequences from the SKCa3-1a transcript of the SK3 gene are disclosed. These sequences are set forth as SEQ ID NO:1 and SEQ ID NO:3.

BRIEF DESCRIPTION OF THE DRAWINGS

FIG. 1 is an illustration of the structures of SKCa3-1a, SKCa3-1b and SKCa3-1c. The figure shows the exons 1–8 in the structure of hSKCa3. The traditional transcript of hSKCa3 is shown as SKCa3-1a and shows the use of exon 1a. Variants SKCa3-1b and SKCa3-1c use exons 1b and 1c, respectively, in place of exon 1a in SKCa3-1a.

FIG. 2 is the full length isoform variant SKCa3-1b (SEQ ID NO: 2), assigned Genbank Accession No. AY138900, which lacks the N-terminus and S1 transmembrane segment of KCNN3 cDNA (referred to herein as SKCa3-1a) and replaces the exon 1a of SKCa3-1a with exon 1b. The figure also includes the nucleotide structure of exon 1b (SEQ ID NO: 1), assigned Genbank Accession No. AY138901.

FIG. 3 is the full length isoform variant SKCa3-1c (SEQ ID NO: 4) assigned Genbank Accession No. AF438203, which lacks the N-terminus and S1 transmembrane segment of KCNN3 cDNA (referred to herein as SKCa3-1a) and replaces the exon 1a of SKCa3-1A with exon 1c. The figure also includes the nucleotide structure of exon 1c (SEQ ID NO: 3), assigned Genbank Accession No. AF438202.

FIG. 4 is a comparison of the expression levels of SKCa3 variants in human tissue, as set forth in Examples 8 and 9. FIGS. 4A–C show pooled human tissues, while FIGS. 4D–F show brain regions from a single donor.

FIG. 5A is a graph of currents produced by SKCa3-1a with GFP, SKCa3-1a with SKCa3-1b and SKCa3-1a with SKCa3-1c, as set forth in Example 1. FIG. 5B is a graph demonstrating the ability of SKCa3-1b to selectively produce dominant-negative suppression of endogenous currents produced by SKCa3-1a, as set forth in Example 10. The SKCa3-1b constructs work comparably whether or not they carry a GFP tag. They do not interfere with other types of potassium channel currents. The SKCa3-1b isoform functions comparably with SKCa3-1b.

FIG. 7 is the genomic organization, splice junctions and putative protein products of SK3 and SKCa3-1b. FIG. 7A is the exon-intron organization of the SK3 locus showing the location of exon 1B. The SK3 and SKCa3-1b cDNAs are also shown. FIG. 7B are the 5' and 3' boundaries of the introns that lie between exons 1, 1B and 2. FIG. 7C is the putative protein product of SK3 showing transmembrane segments, the calmodulin (CAM)-binding site in the C-terminus, and the polyglutamine repeats in the N-terminus. An arrow indicates the presumed start site of SK3-1B.

FIG. 8A shows that SK but not $K_v$ current is blocked by 100 nM apamin. FIG. 8B shows that in the absence of internal $Ca^{2+}$ in the pipette solution SK currents are not visible but $K_v$ currents remain unchanged. FIGS. 8C and 8D show that SKCa3-1b-GFP and SKCa3-1b-IRES-GFP suppress SK but not $K_v$ currents. FIGS. 8E and 8F show that GFP- and GFP-Kv1.7 do not affect SK and $K_v$ currents.

FIG. 9A shows SK2 and Kv1.3 currents in untransfected Jurkat T lymphocytes. FIG. 9B shows SK2 and Kv1.3 currents in SK3-1B-GFP transfected Jurkat T lymphocytes. FIG. 9C shows SK2 and Kv1.3 currents in GFP transfected Jurkat T lymphocytes cells.

FIG. 10A shows untransfected PC12 cells immunolabeled with anti-SK3 antibody, intensity histogram of SK3 fluorescence. FIG. 10B shows SK3-1B-GFP-transfected cells stained for SK3, intensity histogram of SK3 fluorescence. FIG. 10C shows GFP-vector transfected cell, intensity histogram of SK3 fluorescence resembles that of untransfected cells. FIG. 10D shows GFP-Kv1.7-transfected cell, normal intensity histogram. The average intensity histograms shown are based on data derived from 6 cells.

DETAILED DESCRIPTION OF THE INVENTION

Figure 4G:
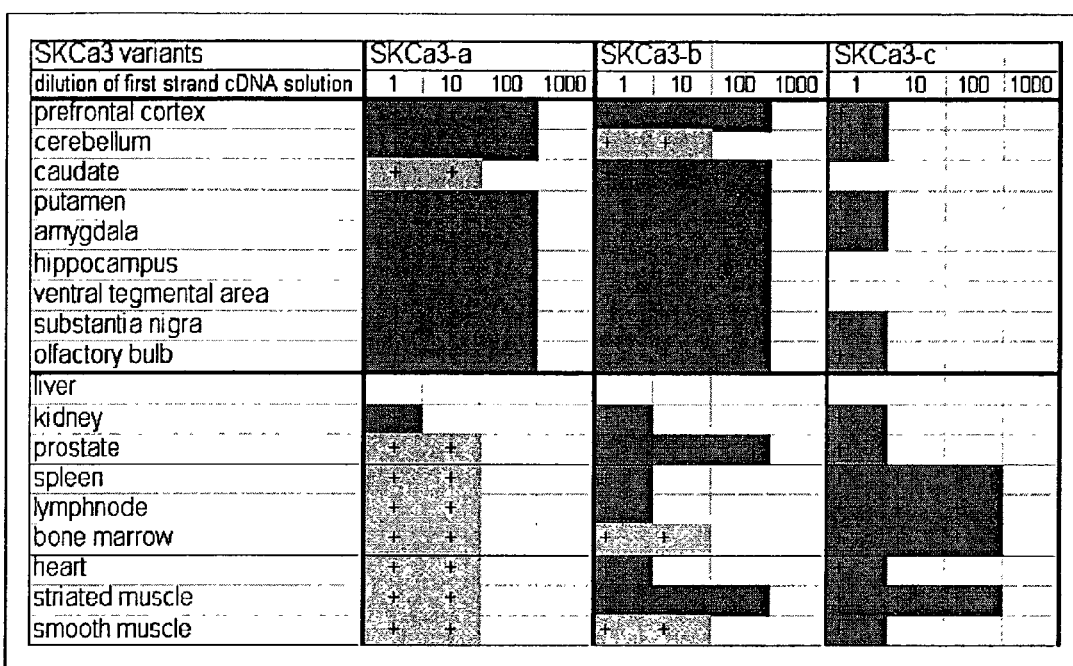
FIG. 4G shows the results in various tissues.

The present invention is based on the discovery of novel isoform variants, SKCa-1b and SKCa3-1c, of the KCNN3 gene (referred to herein as SK3). The SK3 gene is located on human chromosome 1q21 in a region containing a major susceptibility locus for familial schizophrenia and familial hemiplegic migraine associated with permanent cerebellar ataxia. SK3 is expressed abundantly in the regions implicated in schizophrenia including the hippocampus, the limbic system and midbrain regions rich in monoaminergic neurons.

In one embodiment, the invention provides novel isoform variants of the SK3 gene. The variants are referred to herein as SKCa3-1b and SKCa3-1c. The SKCa3-1b variant has a sequence exemplified by a sequence as set forth in SEQ ID NO: 2, containing a 1b exon as set forth in SEQ ID NO: 1. An exemplary SKCa3-1c variant has a sequence as set forth in SEQ ID NO: 4, containing a 1c exon as set forth in SEQ ID NO: 3. The two variants SKCa3-1b and SKCa3-1c differ from the previously disclosed SKCa3-1a transcript of the SK3 gene in lacking the N-terminus and S1 transmembrane segment of SKCa3-1a, and in utilizing exons 1b and 1c in place of exon 1a. The two variants share exons 2 through 8 with the SKCa3-1a isoform. FIG. 1 is a comparative illustration of the structures of SKCa3-1a, SKCa3-1b and SKCa3-1c.

It is noted that while the published sequence Genbank Accession No. AF336797 contains the sequences of the exons of the two variants SKCa3-1b and SKCa3-1c within intron 1 of that sequence, the presence of the exons has not been annotated or otherwise predicted. Comparison of the SK3-1b cDNA sequence with published genomic sequences Genbank Accession Nos.: AF336797, AC034149, AC027645, AC025385 revealed the specific intron-exon organization of SKCa3-1b, as shown in FIG. 7A. Novel exon 1b is located 712 bp downstream from exon 1a, which splices to exon 2, as can be seen in FIGS. 7A and 7B. The splice donor and acceptor sites at the boundaries of the intervening sequences between exons 1, 1b and 2 are shown in FIG. 7B. Exon 1a encodes the 5' non-coding sequence, the entire N terminus and the S1 transmembrane domain of SK3, while exon-1b encodes only the 5' non-coding sequence of SK3-1B; the initiation codon for the SK3-1B isoform is contained in exon 2. The putative protein products of SK3 and SKCa3-1b are shown in FIG. 7C. The SK3 protein (736 residues) is made up of a long N-terminus containing two polymorphic polyglutamine repeats, six transmembrane segments (S1–S6) and a C-terminus tightly complexed to calmodulin. In contrast, the putative SK3-1B protein (418 residues) begins in the same reading frame as SK3, but at the first methionine residue encoded by exon 2, eight residues upstream of the S2 transmembrane segment. It is therefore shown to lack the N-terminus and S1 segments of SK3, as seen in FIG. 7B.

The term "exon" as used herein refers to a region of the DNA of a gene that codes for the proteins of the gene. Exons are intermingled with introns, which are non-coding sequences in the DNA. The introns are subsequently eliminated by splicing when the DNA is translated into mRNA.

The term "polynucleotide" or "nucleic acid sequence" refers to a polymeric form of nucleotides at least 10 bases in length. By "isolated polynucleotide" is meant a polynucleotide that is not immediately contiguous with both of the coding sequences with which it is immediately contiguous (one on the 5' end and one on the 3' end) in the naturally occurring genome of the organism from which it is derived. The term therefore includes, for example, a recombinant DNA which is incorporated into a vector; into an autonomously replicating plasmid or virus; or into the genomic DNA of a prokaryote or eukaryote, or which exists as a separate molecule (e.g., a cDNA) independent of other sequences. The nucleotides of the invention can be ribonucleotides, deoxyribonucleotides, or modified forms of either nucleotide. The term includes single and double forms of DNA.

The polynucleotides encoding the variants of KCNN3 include SEQ ID NOS: 2, 4, dominant negative forms of SKCa3-1b or SKCa3-1c, and nucleic acid sequences complementary to SEQ ID NOS: 2 and 4. A complementary sequence may include an antisense nucleotide. When the sequence is RNA, the deoxynucleotides A, G, C, and T of SEQ ID NO: 2 or 4 are replaced by ribonucleotides A, G, C, and U, respectively. Also included in the invention are fragments of the above-described nucleic acid sequences that are at least 15 bases in length, which is sufficient to permit the fragment to selectively hybridize to DNA that encodes the protein encoded by SEQ ID NOS: 2 and 4 under physiological conditions or a close family member of SKCa3-1B or SKCa3-1C. The term "selectively hybridize" refers to hybridization under moderately or highly stringent conditions which excludes non-related nucleotide sequences.

In nucleic acid hybridization reactions, the conditions used to achieve a particular level of stringency will vary, depending on the nature of the nucleic acids being hybridized. For example, the length, degree of complementarity, nucleotide sequence composition (e.g., GC v. AT content), and nucleic acid type (e.g., RNA v. DNA) of the hybridizing regions of the nucleic acids can be considered in selecting hybridization conditions. An additional consideration is whether one of the nucleic acids is immobilized, for example, on a filter.

An example of progressively higher stringency conditions is as follows: 2×SSC/0.1% SDS at about room temperature (hybridization conditions); 0.2×SSC/0.1% SDS at about room temperature (low stringency conditions); 0.2×SSC/0.1% SDS at about 42° C. (moderate stringency conditions); and 0.1×SSC at about 68° C. (high stringency conditions). Washing can be carried out using only one of these conditions, e.g., high stringency conditions, or each of the conditions can be used, e.g., for 10–15 minutes each, in the order listed above, repeating any or all of the steps listed. However, as mentioned above, optimal conditions will vary, depending on the particular hybridization reaction involved, and can be determined empirically.

It is understood that all polynucleotides encoding SKCa3-1B or SKCa3-1C are also included herein, as long as they encode a polypeptide which functions in a dominant-negative manner to suppress $SK_{Ca}$ currents. Such polynucleotides include naturally occurring, synthetic, and intentionally manipulated polynucleotides. For example, SKCa3-1b or SKCa3-1c polynucleotide may be subjected to site-directed mutagenesis. The polynucleotide sequence for SKCa3-1b or SKCa3-1c also includes antisense sequences, and sequences encoding dominant negative forms of SKCa3-1B or SKCa3-1C. The polynucleotides of the invention include sequences that are degenerate as a result of the genetic code. There are 20 natural amino acids, most of which are specified by more than one codon. Therefore, all degenerate nucleotide sequences are included in the invention as long as the amino acid sequence of SKCa3-1B or SKCa3-1C polypeptide encoded by the nucleotide sequence is functionally unchanged.

The nucleotide sequence encoding the SKCa3-1B or SKCa3-1C polypeptide of the invention includes the disclosed sequence and conservative variations thereof. The term "conservative variation" as used herein denotes the replacement of an amino acid residue by another, biologically similar residue. Examples of conservative variations include the substitution of one hydrophobic residue such as isoleucine, valine, leucine or methionine for another, or the substitution of one polar residue for another, such as the substitution of arginine for lysine, glutamic for aspartic acid, or glutamine for asparagine, and the like. The term "conservative variation" also includes the use of a substituted amino acid in place of an unsubstituted parent amino acid provided that antibodies raised to the substituted polypeptide also immunoreact with the unsubstituted polypeptide.

The invention also provides substantially purified SK3 polypeptides encoded by the SKCa3-1b and SKCa3-1c genomic DNA sequences. The term "substantially purified" as used herein refers to a polypeptide which is substantially free of other proteins, lipids, carbohydrates or other materials with which it is naturally associated. One skilled in the art can purify SKCa3-1B or SKCa3-1C using standard techniques for protein purification. The purity of the SK3 polypeptide can also be determined by amino-terminal amino acid sequence analysis.

Minor modifications of the SKCa3-1B or SKCa3-1C primary amino acid sequences may result in proteins which have substantially equivalent activity as compared to the unmodified counterpart polypeptide described herein. Such modifications may be deliberate, as by site-directed mutagenesis, or may be spontaneous. All of the polypeptides produced by these modifications are included herein as long as the biological activity of the SKCa3-1B or SKCa3-1C still exists.

DNA sequences encoding SKCa3-1B or SKCa3-1C can be expressed in vitro by DNA transfer into a suitable host cell. "Host cells" are cells in which a vector can be propagated and its DNA expressed. The cell may be prokaryotic or eukaryotic. The term also includes any progeny of the subject host cell. It is understood that all progeny may not be identical to the parental cell since there may be mutations that occur during replication. However, such progeny are included when the term "host cell" is used. Methods of stable transfer, meaning that the foreign DNA is continuously maintained in the host, are known in the art.

In the present invention, the SKCa3-1b or SKCa3-1c polynucleotide sequences may be inserted into an expression vector. The term "expression vector" refers to a plasmid, virus or other vehicle known in the art that has been manipulated by insertion or incorporation of the SKCa3-1b or SKCa3-1c genetic sequences. Polynucleotide sequence which encode SKCa3-1B or SKCa3-1C can be operatively linked to expression control sequences. "Operatively linked" refers to a juxtaposition wherein the components so described are in a relationship permitting them to function in their intended manner. An expression control sequence operatively linked to a coding sequence is ligated such that expression of the coding sequence is achieved under conditions compatible with the expression control sequences. As used herein, the term "expression control sequences" refers to nucleic acid sequences that regulate the expression of a nucleic acid sequence to which it is operatively linked. Expression control sequences are operatively linked to a nucleic acid sequence when the expression control sequences control and regulate the transcription and, as appropriate, translation of the nucleic acid sequence. Thus expression control sequences can include appropriate promoters, enhancers, transcription terminators, a start codon (i.e., ATG) in front of a protein-encoding gene, splicing signal for introns, maintenance of the correct reading frame of that gene to permit proper translation of mRNA, and stop codons. The term "control sequences" is intended to included, at a minimum, components whose presence can influence expression, and can also include additional components whose presence is advantageous, for example, leader sequences and fusion partner sequences. Expression control sequences can include a promoter.

By "promoter" is meant minimal sequence sufficient to direct transcription. Also included in the invention are those promoter elements which are sufficient to render promoter-dependent gene expression controllable for cell-type specific, tissue-specific, or inducible by external signals or agents; such elements may be located in the 5' or 3' regions of the gene. Both constitutive and inducible promoters, are included in the invention (see e.g., Bitter et al., *Methods in Enzymology* 153:516–544, 1987.). For example, when cloning in bacterial systems, inducible promoters such as pL of bacteriophage γ, plac, ptrp, ptac (ptrp-lac hybrid promoter) and the like may be used. When cloning in mammalian cell systems, promoters derived from the genome of mammalian cells (e.g., metallothionein promoter) or from mammalian viruses (e.g., the retrovirus long terminal repeat; the adenovirus late promoter; the vaccinia virus 7.5K promoter) may be used. Promoters produced by recombinant DNA or synthetic techniques may also be used to provide for transcription of the nucleic acid sequences of the invention.

In the present invention, the polynucleotide encoding SKCa3-1B or SKCa3-1C may be inserted into an expression vector that contains a promoter sequence that facilitates the efficient transcription of the inserted genetic sequence of the host. The expression vector typically contains an origin of replication, a promoter, as well as specific genes that allow phenotypic selection of the transformed cells. Vectors suitable for use in the present invention include, but are not limited to the T7-based expression vector for expression in bacteria (Rosenberg et al., *Gene* 56:125, 1987), the pMSXND expression vector for expression in mammalian cells (Lee and Nathans, *J. Biol. Chem.* 263:−3521, 1988) and baculovirus-derived vectors for expression in insect cells. The DNA segment can be present in the vector operably linked to regulatory elements, for example, a promoter (e.g., T7, metallothionein I, or polyhedron promoters).

Polynucleotide sequences encoding SKCa3-1B or SKCa3-1C can be expressed in either prokaryotes or eukaryotes. Hosts can include microbial, yeast, insect and mammalian organisms. Methods of expressing DNA sequences having eukaryotic or viral sequences in prokaryotes are well known in the art. Biologically functional viral and plasmid DNA vectors capable of expression and replication in a host are known in the art. Such vectors are used to incorporate DNA sequences of the invention.

By "transformation" is meant a genetic change induced in a cell following incorporation of new DNA (i.e., DNA exogenous to the cell). Where the cell is a mammalian cell, the genetic change is generally achieved by introduction of the DNA into the genome of the cell (i.e., stable).

By "transformed cell" is meant a cell into which (or into an ancestor of which) has been introduced, by means of recombinant DNA techniques, a DNA molecule encoding SKCa3-1B or SKCa3-1C. Transformation of a host cell with recombinant DNA may be carried out by conventional techniques as are well known to those skilled in the art. Where the host is prokaryotic, such as *E. coli*, competent cells that are capable of DNA uptake can be prepared from cells harvested after exponential growth phase and subsequently treated by the $CaCl_2$ method using procedures well known in the art. Alternatively, $MgCl_2$ or RbCl can be used. Transformation can also be performed after forming a protoplast of the host cell if desired.

When the host is a eukaryote, such methods of transfection of DNA as calcium phosphate co-precipitates, conventional mechanical procedures such as microinjection, electroporation, insertion of a plasmid encased in liposomes, or virus vectors may be used. Eukaryotic cells can also be cotransformed with DNA sequences encoding the variant isoforms of the invention, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein (see for example, *Eukaryotic Viral Vectors*, Cold Spring Harbor Laboratory, Gluzman ed., 1982.).

Isolation and purification of microbial expressed polypeptide, or fragments thereof, provided by the invention, may be carried out by conventional means including preparative chromatography and immunological separations involving monoclonal or polyclonal antibodies.

As used herein, the term "antibody" is used in its broadest sense to include polyclonal and monoclonal antibodies, as well as antigen binding fragments of such antibodies. An antibody useful in a method of the invention, or an antigen binding fragment thereof, is characterized, for example, by having specific binding activity for an epitope. In addition, as discussed above, an antibody of the invention can be an antibody that specifically binds a peptide portion of a polypeptide.

The term "binds specifically" or "specific binding activity," when used in reference to an antibody means that an interaction of the antibody and a particular epitope has a dissociation constant of at least about $1 \times 10^{-6}$, generally at least about $1 \times 10^{-7}$, usually at least about $1 \times 10^{-8}$, and particularly at least about $1 \times 10^{-9}$ or $1 \times 10^{-10}$ or less. As such, Fab, $F(ab')_2$, Fd and Fv fragments of an antibody that retain specific binding activity for a SKCa3-1B or SKCa3-1C polypeptide of the invention, are included within the definition of an antibody.

The term "antibody" as used herein includes naturally occurring antibodies as well as non-naturally occurring antibodies, including, for example, single chain antibodies, chimeric, bifunctional and humanized antibodies, as well as antigen-binding fragments thereof. Such non-naturally occurring antibodies can be constructed using solid phase peptide synthesis, can be produced recombinantly or can be obtained, for example, by screening combinatorial libraries consisting of variable heavy chains and variable light chains (see Huse et al., *Science* 246:1275–1281 (1989).). These and other methods of making, for example, chimeric, humanized, CDR-grafted, single chain, and bifunctional antibodies are well known to those skilled in the art (Winter and Harris, *Immunol. Today* 14:243–246, 1993; Ward et al., *Nature* 341:544–546, 1989; Harlow and Lane, Antibodies: A laboratory manual (Cold Spring Harbor Laboratory Press, 1988); Hilyard et al., *Protein Engineering: A practical approach* (IRL Press 1992); Borrabeck, *Antibody Engineering, 2d ed.* (Oxford University Press 1995).).

If desired, a kit incorporating an antibody or other agent useful in a method of the invention can be prepared. Such a kit can contain, in addition to the agent, a pharmaceutical composition in which the agent can be reconstituted for administration to a subject. The kit also can contain, for example, reagents for detecting the antibody, or for detecting specific binding of the antibody to a desired protein. Such detectable reagents useful for labeling or otherwise identifying the antibody are described herein and known in the art.

Methods for raising polyclonal antibodies, for example, in a rabbit, goat, mouse or other mammal, are well known in the art (see, for example, Green et al., "Production of Polyclonal Antisera," in *Immunochemical Protocols* (Manson, ed., Humana Press 1992), pages 1–5; Coligan et al., "Production of Polyclonal Antisera in Rabbits, Rats, Mice and Hamsters," in *Curr. Protocols Immunol.* (1992), section 2.4.1.). In addition, monoclonal antibodies can be obtained using methods that are well known and routine in the art (Harlow and Lane, supra, 1988). For example, spleen cells from a mouse immunized with SKCa3-1B or SKCa3-1C, or an epitopic fragment thereof, can be fused to an appropriate myeloma cell line such as SP/02 myeloma cells to produce hybridoma cells. Cloned hybridoma cell lines can be screened using labeled antigen to identify clones that secrete monoclonal antibodies having the appropriate specificity, and hybridomas expressing antibodies having a desirable specificity and affinity can be isolated and utilized as a continuous source of the antibodies. The antibodies can be further screened for the inability to bind specifically with the cytokine or cytokine receptor. Such antibodies are useful, for example, for preparing standardized kits for clinical use. A recombinant phage that expresses, for example, a single chain antibody also provides an antibody that can used for preparing standardized kits.

Methods of preparing monoclonal antibodies well known (see, for example, Kohler and Milstein, *Nature* 256:495, 1975; see, also, Coligan et al., supra, 1992, see sections 2.5.1–2.6.7; Harlow and Lane, supra, 1988). Briefly, monoclonal antibodies can be obtained by injecting mice with a composition comprising an antigen, verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures.

Monoclonal antibodies can be isolated and purified from hybridoma cultures by a variety of well established techniques, including, for example, affinity chromatography with Protein-A SEPHAROSE, size exclusion chromatography, and ion exchange chromatography (Coligan et al., supra, 1992, see sections 2.7.1–2.7.12 and sections 2.9.1–2.9.3; see, also, Barnes et al., "Purification of Immunoglobulin G (IgG)," in *Meth. Molec. Biol.* 10:79–104 (Humana Press 1992).). Methods of in vitro and in vivo multiplication of monoclonal antibodies is well known to those skilled in the art. Multiplication in vitro can be carried out in suitable culture media such as Dulbecco's Modified Eagle Medium or RPMI 1640 medium, optionally replenished by a mammalian serum such as fetal calf serum or trace elements and growth sustaining supplements such as normal mouse peritoneal exudate cells, spleen cells, bone marrow macrophages. Production in vitro provides relatively pure antibody preparations and allows scale-up to yield large amounts of the desired antibodies. Large scale hybridoma cultivation can be carried out by homogenous suspension culture in an airlift reactor, in a continuous stirrer reactor, or in immobilized or entrapped cell culture. Multiplication in vivo can be carried out by injecting cell clones into mammals histocompatible with the parent cells, for example, syngeneic mice, to cause growth of antibody producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Therapeutic applications for antibodies disclosed herein are also part of the present invention. For example, antibodies of the present invention can also be derived from subhuman primate antibody. General techniques for raising therapeutically useful antibodies in baboons can be found, for example, in Goldenberg et al., International Patent Publication WO 91/11465 (1991); and Losman et al., *Int. J. Cancer* 46:310, 1990.

A therapeutically useful antibody also can be derived from a "humanized" monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are known (see, for example, Orlandi et al., *Proc. Natl. Acad. Sci., USA* 86:3833, 1989.). Techniques for producing humanized monoclonal antibodies also are known (see, for example, Jones et al., *Nature* 321:522, 1986; Riechmann et al., *Nature* 332:323, 1988; Verhoeyen et al., *Science* 239:1534, 1988; Carter et al., *Proc. Natl. Acad. Sci., USA* 89:4285, 1992; Sandhu, *Crit. Rev. Biotechnol.* 12:437, 1992; and Singer et al., *J. Immunol.* 150:2844, 1993.).

Antibodies of the invention also can be derived from human antibody fragments isolated from a combinatorial immunoglobulin library (see, for example, Barbas et al., *METHODS: A Companion to Methods in Immunology* 2:119, 1991; Winter et al., *Ann. Rev. Immunol.* 12:433, 1994.). Cloning and expression vectors that are useful for producing a human immunoglobulin phage library can be obtained, for example, from STRATAGENE Cloning Systems (La Jolla, Calif.).

An antibody of the invention also can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13, 1994; Lonberg et al., *Nature* 368:856, 1994; and Taylor et al., *Int. Immunol.* 6:579, 1994.

Antibody fragments of the present invention can be prepared by proteolytic hydrolysis of the antibody or by expression in *E. coli* of DNA encoding the fragment. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent, and optionally a blocking group for the sulfhydryl groups resulting from cleavage of disulfide linkages, to produce 3.5S Fab' monovalent fragments. Alternatively, an enzymatic cleavage using pepsin produces two monovalent Fab' fragments and an Fc fragment directly (see, for example, Goldenberg, U.S. Pat. No. 4,036,945 and U.S. Pat. No. 4,331,647; and references contained therein; Nisonhoff et al., *Arch. Biochem. Biophys.* 89:230. 1960; Porter, *Biochem. J.* 73:119, 1959; Edelman et al., *Meth. Enzymol.*, 1:422 (Academic Press 1967); see, also, Coligan et al., supra, 1992, see sections 2.8.1–2.8.10 and 2.10.1–2.10.4).

Other methods of cleaving antibodies, such as separation of heavy chains to form monovalent light/heavy chain fragments, further cleavage of fragments, or other enzymatic, chemical, or genetic techniques can also be used, provided the fragments specifically bind to the antigen that is recognized by the intact antibody. For example, Fv fragments comprise an association of $V_H$ and $V_L$ chains. This association can be noncovalent (Inbar et al., *Proc. Natl. Acad. Sci., USA* 69:2659, 1972). Alternatively, the variable chains can be linked by an intermolecular disulfide bond or cross-linked by chemicals such as glutaraldehyde (Sandhu, supra, 1992). Preferably, the Fv fragments comprise $V_H$ and $V_L$ chains connected by a peptide linker. These single-chain antigen binding proteins (sFv) are prepared by constructing a structural gene comprising DNA sequences encoding the $V_H$ and $V_L$ domains connected by an oligonucleotide. The structural gene is inserted into an expression vector, which is subsequently introduced into a host cell such as *E. coli*. The recombinant host cells synthesize a single polypeptide chain with a linker peptide bridging the two V domains. Methods for producing sFvs are described, for example, by Whitlow et al., Methods: A Companion to Methods in Enzymology 2:97, 1991; Bird et al., *Science* 242:423–426, 1988; Ladner et al., U.S. Pat. No. 4,946,778; Pack et al., *Bio/Technology* 11:1271–1277, 1993; see, also Sandhu, supra, 1992.

Another form of an antibody fragment is a peptide coding for a single complementarity-determining region (CDR). CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (see, for example, Larrick et al., *Methods: A Companion to Methods in Enzymology* 2:106, 1991.).

Antibodies (immunoglobulins) are proteins produced by one class of lymphocytes (B cells) in response to specific exogenous foreign molecules (antigens). Monoclonal antibodies (mAB), identical immunoglobulin copies which recognize a single antigen, are derived from clones (identical copies) of a single B cell. This technology enables large quantities of an immunoglobulin with a specific target to be mass produced.

Advances in biotechnology have resulted in improved molecules as compared to simply using monoclonal antibodies. One such molecule is an antibody fragment. By removing part of the antibody structure, the function of this molecule is changed so that it acts differently in the human body. Another new type of molecule, distinct from monoclonal antibodies and soluble receptors, is a fusion protein. Such molecules have a distinct function which acts differently in the human body than a simple soluble receptor or receptors.

A search of the National Center for Biotechnology Information (NCBI) EST database that contains sequence data and other information on "single-pass" cDNA sequences, or Expressed Sequence Tags ("ESTs"), from a number of organisms revealed at least five independent ESTs in the database that correspond to portions of SKCa3-1c. The ESTs found were derived mainly from Burkitt's lymphomas and were found to have Genbank Accession numbers: BE562092, BE397619, BE513322 and BE397440.). Additionally, an EST in a rhabdomyosarcoma with Genbank Accession number BF306047 was found to correspond to a portion of SKCa3-1b. As this transcript is present in these tumors in abundance, use of SKCa3-1b or SKCa3-1c as a diagnostic or prognostic marker is another aspect of the invention.

Additionally, it has been found that fluorescently labeled SKCa3-1B and SKCa3-1C trap SKCa3-1A intracellularly. Generally, when expressed in isolation in mammalian cells, GFP-SKCa3-1A is distributed throughout the cell, especially in the plasma membrane. In contrast, fluorescently labeled SKCa3-1B and SKCa3-1C both localize intracellularly in presumptive ER and golgi. When co-expressed with GFP-SKCa3-1A, either fluorescently labeled SKCa3-1B or fluorescently labeled SKCa3-1C trap GFP-SKCa3-1A intracellularly. The intracellular trapping underlies the dominant-negative suppression of SKCa3-1a current described above.

SKCa3-1b and SKCa3-1c also negative dominantly suppress GFP-SKCa1 currents expressed in mammalian cells.

Further SKCa3-1b and SKCa3-1c negative dominantly suppress endogenous $SK_{Ca}$ channels in PC-12 cells. GFP-SKCa1 produces robust calcium-activated currents when expressed in COS-7 cells (Shakkottai et al., *J. Biol. Chem.* 276 (46): 43145–43151, 2001.). When co-expressed with fluorescently labeled SKCa3-1b (Tomita et al, 2002 *Mol. Psych.* In press) or fluorescently labeled SKCa3-1c, dominant-negative suppression of SKCa3-1a is seen. Similarly, fluorescently labeled SKCa3-1b (Tomita et al, 2002 *Mol. Psych.* In press) and fluorescently labeled SKCa3-1c dominant-negatively suppress endogenous $SK_{Ca}$ currents present in PC12 cells (Sun et al., *J. Hum. Genet.* 46, 463–470, 2001.).

Figure 6:
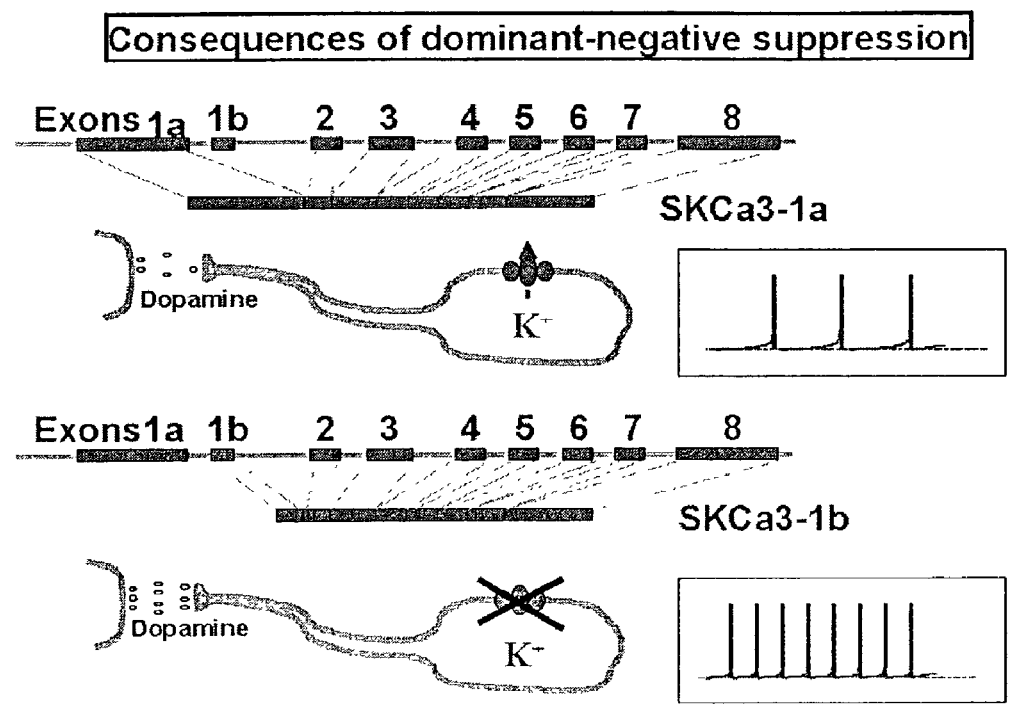
FIG. 6 is an illustration of the potential consequence of dominant negative suppression of $SK_{Ca}$ currents and its implication for schizophrenia.

Enhanced expression of SKCa3-1b and SKCa3-1c would alter the functional/non-functional ratio for $SK_{Ca}$ channels. Dominant-negative suppression by SKCa3-1b or SKCa3-1c could lead to global reduction of the entire family of $SK_{Ca}$ channels, causing inhibition of post-spike AHP. Inhibition of post-spike AHP would lead to a change in the firing pattern of dopaminergic neurons from a pacemaker-like discharge as described above to a multiple bursting pattern. Such a bursting pattern has a concomitant increase in dopamine release, characteristic of schizophrenia. These changes are diagrammed in FIG. 6.

Such abnormal enhancement of SKCa3-1b or SKCa3-1c expression may be due to mutations of their promoters, or to changes in transcription factors, splicing machinery, message degradation/stabilization machinery and others, either by direct mutations in these genes or in genes controlling them.

The present invention identifies variant polynucleotide sequences SKCa3-1b and SKCa3-1c, which may be expressed in an altered manner as compared to expression of SKCa3-1a in a normal cell, therefore it is possible to design appropriate therapeutic or diagnostic techniques directed to this sequence. As set forth above, expression of SKCa3-1b and/or SKCa3-1c dominantly-negatively suppresses SKCa3-1a. Accordingly, the antibodies and polynucleotides of the invention can be used to detect an SKCa3-1B-associated or SKCa3-1C-associated $SK_{Ca}$ channel dysfunction disorder.

Detection of elevated levels of SKCa3-1b (Tomita et al, 2002 *Mol. Psych.* In press) or SKCa3-1c expression is accomplished by hybridization of nucleic acids isolated from a cell of interest with an SKCa3-1b or SKCa3-1c polynucleotide of the invention. Analysis methods, such as quantitative PCR (Taqman) or Northern Blot analysis, are utilized to quantitate expression of the SKCa3-1b or SKCa3-1c. Other standard nucleic acid detection techniques will be known to those of skill in the art.

Treatment can include modulation of SKCa3-1b or SKCa3-1c gene expression and SKCa3-1B or SKCa3-1C activity by administration of a therapeutically effective amount of a reagent that modulates the SKCa3-1B or SKCa3-1C. Where a disorder is associated with the increased expression of SKCa3-1b or SKCa3-1c, nucleic acid sequences that interfere with the expression of SKCa3-1b or SKCa3-1c can be used. This approach utilizes, for example, antisense nucleic acid, ribozymes, or triplex agents to block transcription or translation of SKCa3-1b or SKCa3-1c mRNA, either by masking that mRNA with an antisense nucleic acid or triplex agent, or by cleaving it with a ribozyme. Alternatively, therapeutic methods may be directed to the stimulation of $SK_{Ca}$ channel function in response to the suppression of SKCa3-1a and the subsequent $SK_{Ca}$ channel dysfunction. Specifically, regulation of SK3 and SK3-1B levels may provide a potent mechanism to titrate neuronal firing rates and neurotransmitter release in monoaminergic neurons, and alterations in the relative abundance of these proteins could contribute to abnormal neuronal excitability, and to the pathogenesis of schizophrenia or other $SK_{Ca}$ related disorders. (Coghlan M. J., Carrol W. A., Gopalakrishnan M. (2001). *J. Med. Chem.* 44: 1627–1653; Shich C.-C., Coghlan M., Sullivan J., Gopalakrishnan M., *Pharmacological Reviews* 52: 557–593, 2000; Cao et al., *J. Pharm. Exp. Ther.* 296, 683–689, 2001.)

Various viral vectors which can be utilized for gene therapy as taught herein include adenovirus, herpes virus, vaccinia, or, preferably, an RNA virus such as a retrovirus. Preferably, the retroviral vector is a derivative of a murine or avian retrovirus. Examples of retroviral vectors in which a single foreign gene can be inserted include, but are not limited to: Moloney murine leukemia virus (MoMuLV), Harvey murine sarcoma virus (HaMuSV), murine mammary tumor virus (MuMTV), and Rous Sarcoma Virus (RSV). Preferably, when the subject is a human, a vector such as the gibbon ape leukemia virus (GaLV) is utilized. A number of additional retroviral vectors can incorporate multiple genes. All of these vectors can transfer or incorporate a gene for a selectable marker so that transduced cells can be identified and generated. By inserting a SKCa3-1b or SKCa3-1c sequence of interest into the viral vector, along with another gene which encodes the ligand for a receptor on a specific target cell, for example, the vector is now target specific. Retroviral vectors can be made target specific by attaching, for example, a sugar, a glycolipid, or a protein. Preferred targeting is accomplished by using an antibody to target the retroviral vector. Those of skill in the art will know of, or can readily ascertain without undue experimentation, specific polynucleotide sequences which can be inserted into the retroviral genome or attached to a viral envelope to allow target specific delivery of the retroviral vector containing the SKCa3-1b or SKCa3-1c polynucleotide.

Since recombinant retroviruses are defective, they require assistance in order to produce infectious vector particles. This assistance can be provided, for example, by using helper cell lines that contain plasmids encoding all of the structural genes of the retrovirus under the control of regulatory sequences within the LTR. These plasmids are missing a nucleotide sequence which enables the packaging mechanism to recognize an RNA transcript for encapsidation. Helper cell lines which have deletions of the packaging signal include, but are not limited to Q2, PA317, and PA12, for example. These cell lines produce empty virions, since no genome is packaged. If a retroviral vector is introduced into such cells in which the packaging signal is intact, but the structural genes are replaced by other genes of interest, the vector can be packaged and vector virion produced.

Alternatively, NIH 3T3 or other tissue culture cells can be directly transfected with plasmids encoding the retroviral structural genes gag, pol and env, by conventional calcium phosphate transfection. These cells are then transfected with the vector plasmid containing the genes of interest. The resulting cells release the retroviral vector into the culture medium.

Another targeted delivery system for the therapeutic polynucleotides is a colloidal dispersion system. Colloidal dispersion systems include macromolecule complexes, nanocapsules, microspheres, beads, and lipid-based systems including oil-in-water emulsions, micelles, mixed micelles, and liposomes. The preferred colloidal system of this invention is a liposome. Liposomes are artificial membrane vesicles which are useful as delivery vehicles in vitro and in vivo. It has been shown that large unilamellar vesicles (LUV), which range in size from 0.2–4.0 µm can encapsulate a substantial percentage of an aqueous buffer containing large macromolecules. RNA, DNA and intact virions can be encapsulated within the aqueous interior and be delivered to cells in a biologically active form (Fraley et al., 1981, *Trends Biochem. Sci.* 6:77, 1981.). In addition to mammalian cells, liposomes have been used for delivery of polynucleotides in plant, yeast and bacterial cells. In order for a liposome to be an efficient gene transfer vehicle, the following characteristics should be present: (1) encapsulation of the genes of interest at high efficiency while not compromising their biological activity; (2) preferential and substantial binding to a target cell in comparison to non-target cells; (3) delivery of the aqueous contents of the vesicle to the target cell cytoplasm at high efficiency; and (4) accurate and effective expression of genetic information (Mannino et al., *Biotechniques* 6:682, 1988.).

The composition of the liposome is usually a combination of phospholipids, particularly high-phase-transition-temperature phospholipids, usually in combination with steroids, especially cholesterol. Other phospholipids or other lipids may also be used. The physical characteristics of liposomes depend on pH, ionic strength, and the presence of divalent cations.

Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14–18 carbon atoms, particularly from 16–18 carbon atoms, and is saturated. Illustrative phospholipids include egg phosphatidylcholine, dipalmitoylphosphatidylcholine and distearoylphosphatidylcholine.

The targeting of liposomes can be classified based on anatomical and mechanistic factors. Anatomical classification is based on the level of selectivity, for example, organ-specific, cell-specific, and organelle-specific. Mechanistic targeting can be distinguished based upon whether it is passive or active. Passive targeting utilizes the natural tendency of liposomes to distribute to cells of the reticuloendothelial system (RES) in organs which contain sinusoidal capillaries. Active targeting, on the other hand, involves alteration of the liposome by coupling the liposome to a specific ligand such as a monoclonal antibody, sugar, glycolipid, or protein, or by changing the composition or size of the liposome in order to achieve targeting to organs and cell types other than the naturally occurring sites of localization.

The surface of the targeted delivery system may be modified in a variety of ways. In the case of a liposomal targeted delivery system, lipid groups can be incorporated into the lipid bilayer of the liposome in order to maintain the targeting ligand in stable association with the liposomal bilayer. Various linking groups can be used for joining the lipid chains to the targeting ligand.

Therefore, the present invention also presents a novel therapeutic approach for schizophrenia or other $SK_{Ca}$-related disorder. Such disorders may include, but are not limited to schizophrenia, anorexia nervosa, ataxia, bipolar disorder, autism, migraines and seizures. As the presence of SKCa3-1b or SKCa3-1c may dominantly negatively suppress SKCa3-1a and other functional SK channel family members, agents capable of salvaging or somehow activating $SK_{Ca}$ channel function are therefore useful as therapeutics for such a $SK_{Ca}$-related disorder.

For example, 1-ethyl-2-benzimidazolinone (1-EBIO) and the clinically used centrally-acting skeletal muscle relaxants chlorzoxazone (Parafon Forte DSC, Ortho-McNeill) and Zoxazolamine have been reported to enhance $SK_{Ca}$ and IKCa1 channel opening (Syme et al., *Am. J. Physiol.* 278: C750–C581, 2000; Cao et al., *J. Pharm. Exp. Ther.* 296, 683–689, 2001.). As predicted by the above-described mechanism, zoxazolamine has been reported to decrease neuronal firing rates, dramatically decrease firing variability and induce a pacemaker-like discharge pattern in dopaminergic neurons (Mathews et al., *Brain Res. Bull.* 12, 479–486, 1984; McMillen et al., *J Neural Transm. Gen. Sect.* 89, 11–25, 1992.). Additional agents may include, but are not limited to: benzimidazolone-derivatives, benzoxazolone-derivatives, benzothiazolone-derivatives, diphenyl oxadiazolones and imidazole compounds that modulate ion channel activity. (WO 00/34248; U.S. Pat. No. 5,869,509; EP 93-610022; WO 84/JP452, incorporated by reference herein.)

In one aspect the invention discloses a method for diagnosis of a disorder associated with $SK_{Ca}$ channel dysfunction. The method comprises detection, in a sample from a patient suspected of having the disorder, an abundance of SKCa3-1b, wherein the abundance of SKCa3-1b is indicative of a disorder associated with $SK_{Ca}$ channel dysfunction. Such disorders may include, but are not limited to schizophrenia.

In another aspect, the invention discloses a method for diagnosis of a disorder associated with $SK_{Ca}$ channel dysfunction. The method comprises detection, in a sample from a patient suspected of having the disorder, an abundance of SKCa3-1c wherein the abundance of SKCa3-1c is indicative of a disorder associated with $SK_{Ca}$ channel dysfunction. Such disorders may include, but are not limited to lymphoma, leukemia or cancer.

In still another aspect, the invention discloses a method for treatment of a disorder associated with $SK_{Ca}$ channel dysfunction, wherein the disorder results from expression of SKCa3-1b or SKCa3-1c. The method comprises administration of an agent that activates $SK_{Ca}$ channel function. Disorders that may be treated by the methods of the invention include, but are not limited to, schizophrenia, anorexia nervosa, bipolar disease, autism, migranes and seizures. In one aspect the agent is a benzimidazolone-derivative, benzoxazolone-derivative, benzothiazolone-derivative, diphenyl oxadiazolone or imidazole compound that modulates ion channel activity. In another aspect the agent is 1-ethyl-2-benzimidazolinone, chlorzoxazone or zoxazolamine.

Mechanisms of administration of therapy of the invention include, but are not limited to: i) direct administration of the variants or agents by mucosal, intravenous (iv), subcutaneous (sc), or intramusculatory (im) routes; ii) injection of DNA constructs encoding one or more variants; iii) conditioning ex vivo of relevant cell subtypes (e.g., T or B cells) by SKCa3-1B or SKCa3-1C in the same microenvironment; and iv) administration of antibodies (e.g., human, non-human, and/or chimeric) designed to bind SKCa3-1B or SKCa3-1C. Additional treatments are known to those of skill in the art.

The materials for use in the assay of the invention are ideally suited for the preparation of a kit. Such a kit may comprise a carrier means containing one or more container means such as vials, tubes, and the like, each of the container means comprising one of the separate elements to be used in the method. One of the container means may comprise a probe that is or can be detectably labeled. Such probe may be an antibody or nucleic acid sequence specific for SKCa3-1b, SKCa3-1c, or specific fragments thereof. For example, oligonucleotide probes of the present invention can be included in a kit and used for examining the presence of SKCa3-1b or SKCa3-1c in a sample, as well as the quantitative (relative) degree of binding of the probe for determining the occurrence of specific strongly binding (hybridizing) sequences, thus indicating the likelihood for an subject having or predisposed to a disorder associated with an abundance of SKCa3-1b or SKCa3-1c and/or suppression of SKCa3-1a functions.

The kit may also contain a container comprising a reporter-means, such as a biotin-binding protein, such as avidin or streptavidin, bound to a reporter molecule, such as an enzymatic, fluorescent, or radionucleotide label to identify the detectably labeled oligonucleotide probe.

Where the kit utilizes nucleic acid hybridization to detect the target nucleic acid, the kit may also have containers containing nucleotide(s) for amplification of the target nucleic acid sequence. When it is desirable to amplify the SKCa3-1b or SKCa3-1c target sequence, this can be accomplished using oligonucleotide(s) that are primers for amplification. These oligonucleotide primers are based upon identification of the flanking regions contiguous with the target nucleotide sequence.

The kit may also contain a container containing antibodies that bind to SKCa3-1B or SKCa3-1C, or specific fragments thereof. Such antibodies can be used to distinguish the presence of SKCa3-1B or SKCa3-1C or the level of expression of SKCa3-1b or SKCa3-1c in a specimen. Where the kit utilizes antibodies to detect SKCa3-1B or SKCa3-1C, these antibodies may be directly labeled. The kit may also contain a container containing a reporter means, such as avidin or steptavin bound to a reporter molecule such as an enzymatic, fluorescent, or radionucleotide label to identify the directly labeled antibody. Alternatively, the kit can utilize antibodies that bind SKCa3-1B or SKCa3-1C that are unlabeled. The kit may then also contain a container containing a second antibody that binds to the antibody specific for SKCa3-1B or SKCa3-1C. The second antibody can be directly labeled. The kit may also contain a container containing a reporter means, such as avidin or steptavin, bound to a reporter molecule such as an enzymatic, fluorescent, or radionucleotide label to identify the directly labeled second antibody.

In one aspect of the invention, the kits of the invention are useful for the detection of a target nucleic acid sequence in a sample from a subject having a disorder associated with $SK_{Ca}$ channel dysfunction. In such a detection, the presence of the target nucleic acid sequence in the sample is indicative of having or predisposed to having a human $SK_{Ca}$ channel disorder. As set forth above, the kit contains a carrier means containing one or more containers, wherein a first container contains oligonucleotides which allow amplification of full-length SKCa3-1b or SKCa3-1c nucleic acid sequences such that full-length SKCa3-1b or SKCa3-1c nucleic acid is detected and wherein said full length SKCa3-1b or SKCa3-1c nucleic acid sequence encodes an amino acid sequence that negative dominantly suppresses $SK_{Ca}$ channel function.

Thus the identification of SKCa3-1b or SKCa3-1c within an organism or sample provides a useful tool for diagnosis, prognosis and therapeutic strategies associated with expression of SKCa3-1b or SKCa3-1c and the corresponding suppression of SKCa3-1a in that organism or sample.

The following examples are intended to illustrate but not limit the invention.

EXAMPLE 1

5' Race and Determination of Genomic Organization

The sequence of the SKCa3-1b cDNA was extended by 5'-RACE (Rapid Amplification of cDNA Ends) with an AP1 primer (Clontech, Palo Alto, Calif.) and a SKCa3-1b specific primer (5'-CCTCCATCTCCACTCCCTCTGGGAGGG-3' (SEQ ID NO: 6)), using human adult Marathon-ready™ cDNA (Clontech) as the template. Subsequently, a nested PCR was carried out using the RACE product and an SKCa3-1b specific primer (5'-CCCCTCCTCCGTCT-TGGGGC-3' (SEQ ID NO: 7)) and an AP2 primer (Clontech). The longest product (338 bp) was purified using a QIAQuick™ gel extraction kit, ligated into PCR 2.1 vector and sequenced.

The amplification of the 338 bp product allowed determination of the approximate transcription start site of SKCa3-1b. The composite 1658 bp SKCa3-1b cDNA sequence has been deposited as GenBank Accession No. AY138900) and contains 377 bp of 5' non-coding sequence and a 1254 bp open reading frame.

EXAMPLE 2

Preparation of Total RNA and Real-Time Quantitative RT-PCR

Human Total RNA Master Panel (Clontech) was used to profile the expression pattern of SKCa3-1b. Total RNA was isolated from 9 brain regions of human adult brain tissue using TRIZOL reagent (Life Technologies, Inc.) as per the manufacturer's protocol. Total RNA (1 μg) was used as a template for first-strand cDNA synthesis using poly-T primers (TaqMan reverse transcription reagents, Applied Biosystems). The mRNA for each SK3 transcript was measured by real-time quantitative RT-PCR using a Prism model 7700-sequence detection instrument (PE Applied Biosystems). Forward and reverse primers and TaqMan™ fluorescent probes were designed by Primer Express version 1.5 (Applied Biosystems). Forward primers were designed to anneal to sequences unique to the distinct initial exons of the two SK3 transcripts. The sequences of forward primers were 5'-TGTTATGGTGATAGAGACCGAGCTC-3' (SEQ ID NO: 8) for SK3 and 5'-AGCCCCAAGACGGAGGAG-3' for SKCa3-1b (SEQ ID NO: 9). The reverse primers, designed to anneal to sequences in the shared exon 2, were 5'-TGGACAGACTGATAAGGCATTTCA-3' (SEQ ID NO: 10) for SK3 and 5'-GGCCAACGAAAACATGGAGT-3' (SEQ ID NO: 11) for SKCa3-1b. The TaqMan™ fluorescent probes (5'-labeled with 6FAM, and 3'-labeled with TAMRA as a quencher), designed to anneal to sequences between the forward and reverse primers, were 5'-TGTACTCAAAG-GACTCCATGTTTTCGTTGGC-3' (SEQ ID NO: 12) for SK3 and 5'-TCCCAGAGGGAGTGGAGATGGAGGA-3' (SEQ ID NO: 13) for SKCa3-1b. The SK3 and SKCa3-1b amplification products were 92 bp and 76 bp respectively. The threshold cycle, $C_t$, which correlates inversely with the target mRNA levels, was measured as the cycle number at which the reporter fluorescent emission increased above a pre-set threshold level. To obtain absolute quantification, standard curves were plotted for every assay and were generated using defined concentrations of SKCa3-1b in Image clone 4139388, and SK3 cDNA cloned in pcDNA3.1 HisB. Standard curves for each amplicon were plotted from 8 different concentrations of standards, each run in triplicate.

Concentrations were determined by spectrophotometry and purity confirmed by agarose gel electrophoresis. Purified clones were diluted to eight different concentrations and stored in single-use aliquots at −20° C., and the same diluted preparations were used throughout.

EXAMPLE 3

GFP Constructs

Expressible constructs of the SK3 channel isoforms were produced with C-terminal GFP fluorescent tags to allow facile identification of expressing cells for electrophysiological recording. By inserting in-frame the SKCa3-1b coding region upstream to GFP in the pEGFP-N1 expression vector (Clontech), SKCa3-1b-GFP was generated. A SKCa3-1b construct containing GFP driven by an internal ribosome entry site (SKCa3-1b-IRES-GFP) was also generated by inserting the SKCa3-1b-coding region into the pIRES2-EGFP expression vector (Clontech). The generation of the GFP-tagged Kv1.7 construct and the electrophysiological characterization of this tagged channel have been previously described (Bardien-Kruger et al, *Eur. J. Hum. Genet.* 2002; 10: 36–43.).

EXAMPLE 4

Transfection of Constructs into PC12 and Jurkat Cells

PC12 cells and Jurkat T lymphocytes were obtained from ATCC (Manassas, Va.). PC12 cells were cultured in Dulbecco's modified Eagle's medium containing 10% fetal calf serum and 2 mM glutamine in a 37° C. humidified incubator with 5% $CO_2$ and split 1:10 twice weekly. Jurkat T lymphocytes were cultured in RPMI containing 10% fetal calf serum, 2 mM glutamine and RPMI vitamins. Cells were split 1:4 every two days. Unless otherwise specified, all reagents were obtained from Sigma.

PC12 cells were plated in 12-well plates ($5 \times 10^5$ cells/chamber) for 12–24 h, and then transiently transfected using FuGene™ 6 (Roche Molecular Biochemicals, Indianapolis, Ind.) with the DNA construct of interest in serum-free OptiMEM medium (Life Technologies, Inc.) as per the manufacturer's recommended protocol. Thirty-six hours following transfection, cells were plated for overnight growth on glass coverslips and used for electrophysiological, immunolabeling and confocal microscopy experiments 48 hours post-transfection. Jurkat T lymphocytes were transiently transfected using Xtremegene-Q2 transfection reagent (Roche) as per the manufacturers recommended protocol. Cells were used for electrophysiological analysis 48 hours following transfection.

EXAMPLE 5

Immunostaining

Following washing with DPBS (Dulbecco's phosphate buffered saline), cells were fixed with 4% paraformaldehyde for 20 min and washed 2× with DPBS. Permeabilization and blocking was done with 0.2% Triton-X-100 in 10% normal goat serum, followed by a wash with DPBS. Permeabilized cells were incubated with rabbit anti-SK3 antibody (Alomone Labs, Jerusalem, Israel) in a carrier solution containing 1% normal goat serum and 0.2% sodium azide for 4 hours at 4° C. Cells were subsequently washed and incubated with 1 µg/ml Alexa-Fluor 594 (referred to as Alexa-red)-conjugated goat anti rabbit-IgG (Molecular Probes) for 1 hr at room temperature. The secondary antibody alone showed no signal above background. SK3 antibody specificity was confirmed by pre-incubation of the primary antibody for 1 hr with the blocking peptide supplied by the manufacturer. As an additional test of antibody specificity, the anti-SK3 antibody was shown not to react with SKCa3-1B protein, an isoform that lacks the SK3 N-terminal epitope detected by the antibody. Cells were mounted in 50% glycerol and stored in the dark prior to microscopic analysis.

EXAMPLE 6

Confocal Microscopy

Images were collected with an MRC-1024 laser scanning confocal microscope (Bio-Rad, Hercules, Calif.) on an inverted Nikon Diaphot 200 stand using a 100× oil-immersion objective (Nikon, Melville, N.Y.). Confocal sections through the cell were taken by 1 µM increments of the focus motor. Laser power was maintained at 30% for image acquisition. Excitation wavelengths of 488 and 568 nM were used, and image collection was with 522/35 and 605/32 emission filters. Images were processed with Confocal Assistant™ and Adobe™ Photoshop 5.0.2. The Scion image 4.0.2 program (Scion Corporation, Frederick, Md.) was used to determine the pixel intensity of fluorescence that tagged presumptive intracellular and membrane SK3 protein. Three axes were drawn through each stained cell and pixel intensities were measured along each of these axes. The cell margins were defined as a rise of pixel intensity to 50% above background. The length of the axes between the cell margins was normalized to obtain the average intensity profile for each cell. The mean of the scaled intensity histograms was obtained for six native PC12 cells and six cells transfected with each GFP construct. The average ratio of presumptive membrane to intracellular fluorescence was estimated from these intensity histograms. The expression level of each transfected construct was quantitated as mean pixel intensity.

EXAMPLE 7

Electrophysiology

PC12 and Jurkat T cells were studied in the whole cell configuration of the patch clamp technique with a holding potential of −80 mV. SK and $K_v$ current amplitude were determined in untransfected cells or in cells transfected with SKCa3-1b-GFP, SKCa3-1b-IRES-GFP, or control constructs (GFP vector alone, GFP-Kv1.7). Strategies previously employed for other types of $K^+$ channels were used to determine whether SKCa3-1B could selectively suppress endogenous SK currents without affecting $K_v$ currents (Miller et al, *J. Biol. Chem.* 2001; 276: 27753–27756; Tu et al, *J. Biol. Chem.* 1996; 271:18904–18911; Joiner et al, *J. Biol. Chem.* 2001; 276: 37980–37985; Fanger et al, *J. Biol. Chem.* 2001; 276: 12249–12256; Deutsch, *Annu. Rev. Physiol.*, 2002. 64: 19–46.). This approach relies on the tetrameric structure of $K^+$ channels (Doyle et al, *Science*, 1998. 280: 69–77; Jiang et al, *Nature*, 2002. 417: 523–526; Schumacher et al, *Nature*, 2001. 410: 1120–1124; Jiang et al, *Nature*, 2002. 417: 515–522) and on the ability of SK subunits to co-assemble specifically with other SK subunits (Ishii et al, *J. Biol. Chem.* 1997; 272: 23195–23200.).

SKCa3-1b was over-expressed in PC12 and Jurkat cells to ensure that the majority of SK tetramers would contain at least one SKCa3-1b subunit. Brightly GFP-positive cells were identified under a fluorescence microscope to allow the analysis of cells expressing high levels of the channel constructs for electrophysiological studies. Control constructs were expressed at equivalently high levels as assessed by the intensity of the GFP signal.

To activate SK channels, the pipette solution contained (in mM): 145 $K^+$ aspartate, 2 $MgCl_2$, 10 HEPES, 10 $K_2$EGTA, and 8.5 $CaCl_2$ (1 µM free $Ca^{2+}$), pH 7.2, 290–310 mOsm. The external solution contained (in mM): 160 $K^+$ aspartate (aspartate was used to minimize contributions of $Cl^-$ current), 4.5 KCl, 2 $CaCl_2$, 1 $MgCl_2$, and 5 HEPES, pH 7.4, 290–310 mOsm. SK currents were elicited by 200-ms voltage ramps from −120 to 40 mV applied every 10 s, and slope conductance at −80 mV was taken as a measure of the SK conductance. Block of the SK current with apamin (BACHEM Bioscience Inc., King of Prussia, Pa.) or with Lei-Dab[7] (gift from Jean-Marc Sabatier, University of Marseille) was observed as a reduction in slope conductance at −80 mV. To demonstrate the $Ca^{2+}$ dependence of this current, an internal solution containing calcium free KF was used. The amplitude of the $K_V$ current was measured as the maximum current at 30 mV in 160 $Na^+$ aspartate. Results obtained from untransfected and transfected cells were compared using a Student t-Test.

EXAMPLE 8

Expression Levels of SKCa3 Variants in Human Tissues

The relative abundance of SKCa3-1b and SKCa3-1c compared to SKCa3-1a in various human tissues has been determined using quantitative RT-PCR (TaqMan). SKCa3-1a mRNA distribution in the brain detected by the TaqMan method (see FIG. 4; Tomita et al, *Mol. Psych.* 2002, In press) correlates well with previous data based on in-situ hybrization studies (Dror et al., *Mol. Psych.* 4, 254–260, 1999; Stocker and Pedarzani *Mol. Cell. Neurosci.* 15, 476–493, 2000; Rimini et al., *Brain Res.*, 85, 218–220, 2000; Tacconi et al., *Neurosci.* 102, 209–215, 2001.).

Similarly, the SKCa3-1b and SKCa3-1c mRNA distribution in various tissues was detected by the TaqMan method. The results are set forth in FIG. 4. This figure shows that SKCa3-1b is predominantly expressed in the brain at 15–60% the level of SKCa3-1a, whereas SKCa3-1c is mainly expressed in lymphoid organs (but not peripheral blood lymphocytes) at equivalent levels to SKCa3-1a. Additionally, all three transcripts are shown to be found in skeletal muscle.

EXAMPLE 9

Expression Levels of the SKCa3-1B Variant in the Brain

TaqMan™ quantitative RT-PCR was used to determine the abundance of SK3 and SKCa3-1b transcripts in total RNA derived from tissues pooled from multiple human donors (Clontech). Each cDNA sample was analyzed 3–9 times and the mean copy number (±standard deviation) per µl of cDNA determined (FIG. 4). The expression levels are arbitrarily divided into three groups (defined by horizontal lines in FIGS. 4A and 4B), abundant (>1000 copies/µl cDNA), intermediate (100–1000 copies/µl cDNA) and low (<100 copies/µl cDNA). SK3 is expressed abundantly in adult and fetal brain and uterus, at intermediate levels in skeletal muscle, spleen, thymus, adrenal gland, thyroid, kidney, testis, trachea, and at low levels in bone marrow, fetal and adult liver, heart, lung, placenta, salivary gland and prostate (FIG. 4A). SKCa3-1b is present abundantly in the adult brain, at intermediate levels in fetal brain, cerebellum and uterus, and at lower levels in all the other tissues studied (FIG. 4B). The horizontal lines in FIGS. 4A and 4B show the arbitrary division into abundant, intermediate and low expression levels. The ratio of SKCa3-1B/SK3, displayed as a percentage, is shown in FIG. 4C. In the brain SKCa3-1B is present at between 15–60% of the level of SK3, and at significantly lower levels in other tissues.

TaqMan™ RT-PCR was also performed on SK3 and SKCa3-1b products amplified from total RNA isolated from different brain regions of a single human donor (FIGS. 4D–F). SK3 was highly expressed in the olfactory bulb, putamen, prefrontal cortex, and in dopaminergic neurons in the ventral tegmental area and substantia nigra, and at lower levels in the caudate, amygdala, hippocampus and cerebellum (FIG. 4D), findings consistent with published expression data (Dror et al, *Mol. Psychiatry* 1999; 4: 254–260; Stocker et al. *Mol. Cell Neurosci.* 2000; 15: 476–493; Rimini et al, *Brain Res.* 2000; 85: 218–220.). SKCa3-1B was present in all these regions although at lower levels than SK3 (FIG. 4E). The ratio of SKCa3-1B/SK3 in the different brain areas of this donor varied from 15–60% (FIG. 4F). The high ratio of SKCa3-1B/SK3 in the pooled brain sample is consistent with the overall levels found in the single donor brain regions (compare FIGS. 4C and 4F).

EXAMPLE 10

Selective Expression of SK Currents in PC12 Cells

The rat pheochromocytoma cell line, PC12, was used as the experimental system since these cells natively express SK3 currents (Sun et al, *J. Hum. Genet.* 2001; 46: 463–470.), as well as $K_V$ currents that would serve as an internal control. Two SKCa3-1b constructs were used: SKCa3-1b-GFP and SKCa3-1b-IRES-GFP. As controls, GFP alone or an unrelated GFP-tagged channel (GFP-Kv1.7) were expressed. The expression level of each construct was quantitated as mean pixel intensity. SKCa3-1b-GFP was expressed at a slightly lower level (mean pixel intensity: 108) than GFP-Kv1.7 (mean pixel intensity: 180) or GFP vector alone (mean pixel intensity 174).

Figure 8:
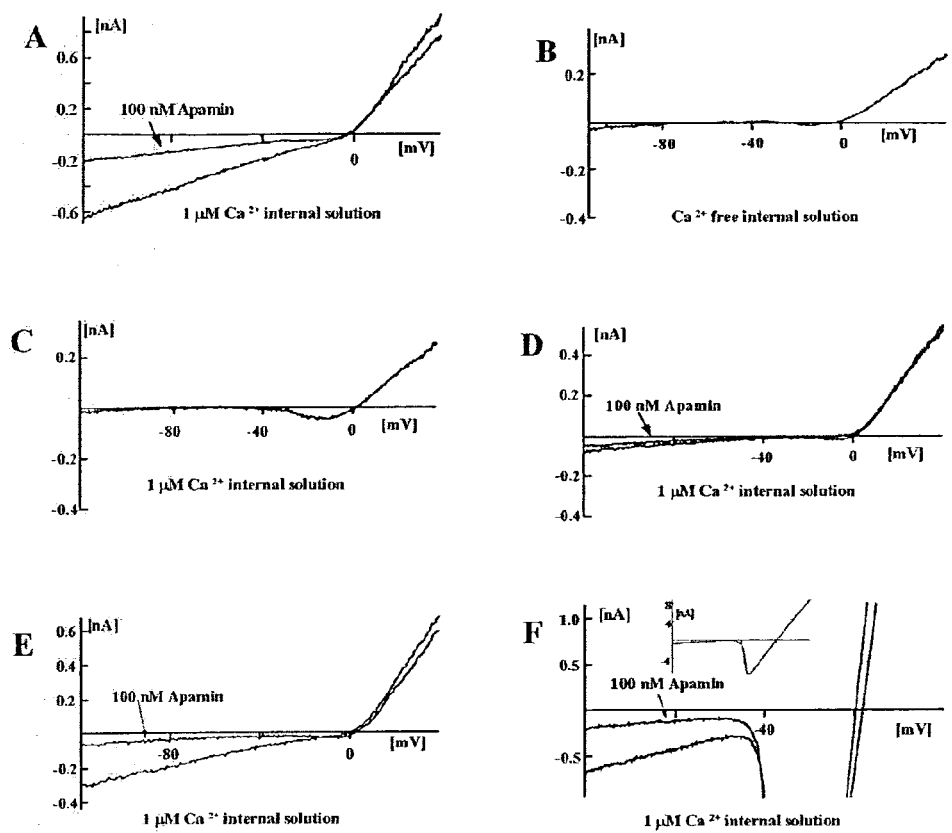
FIG. 8 shows the dominant negative suppression of endogenous SK currents in PC12 cells by SKCa3-1b, as set forth in Example 10.

FIG. 8A demonstrates the endogenous SK3 and $K_V$ currents in PC12 cells. Current traces were elicited by voltage ramps from −80 to 40 mV. At potentials more negative than −40 mV, an inward SK3 current was seen if the pipette contained 1 µM free calcium (FIG. 8A), but was absent when calcium was omitted from the pipette solution (FIG. 8B). The calcium-activated inward SK3 current was selectively blocked by apamin (100 nM), a potent peptide blocker of SK channels (FIG. 8A). The outward $K_V$ current observed at potentials more positive than 0 mV was unaffected by the internal calcium concentration and was not inhibited by apamin. All SK recordings were done with symmetric (160 mM) $K^+$ as internal and external recording solutions. $K_V$ current amplitude was determined with an external solution containing 160 mM $Na^+$ aspartate. The amplitudes of the SK3 and $K_V$ currents varied from cell to cell and are summarized in FIG. 5.

Expression of SKCa3-1b-GFP in PC12 cells abolished the native SK3 current without affecting the endogenous $K_V$ current (compare FIG. 8C with FIG. 8A). Untagged SKCa3-1b in a bicistronic vector containing GFP under translational control of an IRES element (SKCa3-1b-IRES-GFP) had a similar suppressive effect (FIG. 8D). To control for possible artifacts due to transfection and GFP over-expression, patch clamp experiments were performed on PC12 cells transfected with the GFP vector alone. SK currents in GFP-transfected cells were sensitive to apamin and of comparable amplitude to untransfected cells (compare FIG. 8E with FIG. 8A). Patch clamp experiments were also performed on PC12 cells transfected with a GFP-tagged voltage-gated potassium channel, Kv1.7, only distantly related to SK channels, to ensure that dominant-negative suppression by SKCa3-1b was specific (FIG. 8F). In these cells a large Kv1.7 current was seen, which was inward at –40 to 0 mV, and outward beyond 0 mV, consistent with the Nernst potential for potassium. Despite the presence of this substantial $K_v$ current, the amplitude of the apamin-sensitive SK currents (seen at potentials more negative than –40 mV) was indistinguishable from controls. The scatter plot in FIG. 5B summarizes the data and demonstrates that SKCa3-1b-GFP and SKCa3-1b-IRES-GFP selectively suppress endogenous SK currents without affecting $K_v$ currents (means±SEM in FIG. 5B legend). SK currents (mean±SEM) in untransfected (open squares; 6.24±1.57 nS, n=22), SK3-1B-GFP-transfected (open triangles, 0.68±0.08 nS, n=11; p=0.018) and SK3-1B-IRES-GFP-transfected PC12 cells (open circles; 1.1±0.03 nS, n=12; p=0.024). $K_v$ currents (mean±SEM) in untransfected (filled squares; 707.94±147.7 pA, n=15), SK3-1B-GFP-transfected (filled triangles; 475.96±61.78 pA, n=15; p>0.05) and SK3-1B-IRES-GFP-transfected PC12 cells (filled circles; 560.37±75.9 pA, n=14; p>0.05). Together, these results indicate that SKCa3-1b suppresses native SK currents in PC12 cells specifically and in a dominant-negative fashion.

EXAMPLE 11

Dominant Negative Suppression of SKCa3-1A by SKCa3-1B AND SKCa3-1C in Mammalian Cells As can be seen in FIG. 5A, SKCa3-1b negative dominantly suppresses SKCa3-1a currents in mammalian cells. When normally expressed in mammalian cells, native or green fluorescence protein (GFP) tagged SKCa3-1a produces robust apamin- and Leiurus toxin-sensitive calcium-activated currents (Shakkottai et al., *J. Biol. Chem.* 276 (46): 43145–43151, 2001.). Co-expression of SKCa3-1B, either untagged or with a GFP tag, produces a selective dramatic inhibition of this current, leaving voltage-activated potassium currents unaltered. SKCa3-1C produces comparable results (not shown).

EXAMPLE 12

Suppression of Other SK Channels by SKCa3-1B

Figure 9:
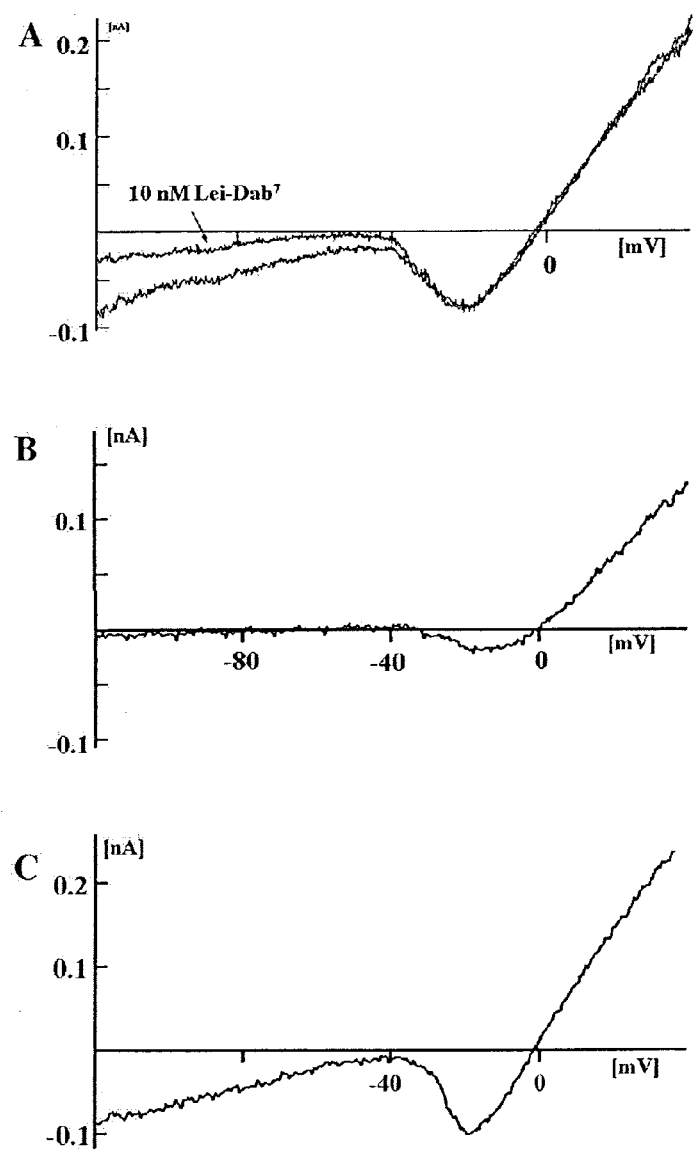
FIG. 9 shows the dominant negative suppression of endogenous SK2 currents in Jurkat T lymphocytes by SK3-1b, as set forth in Example 12.

Human Jurkat T lymphocyte cell line was chosen for these experiments because they express SK2 channels and no other SK channels, along with voltage-gated Kv1.3 channels that could serve as an internal control (Fanger et al, *J. Biol. Chem.* 2001; 276: 12249–12256; Grissmer et al, *J. Gen. Physiol.* 1992; 99: 63–84; Desai et al, *J. Biol. Chem.* 2000; 275: 39954–39963.). Using the electrophysiological protocol described above for PC12 cells, SK2 and Kv1.3 currents in Jurkat cells were measured. The inward SK2 current, detected at potentials more negative than –40 mV, was blocked by Lei-Dab[7] (FIG. 9A), a highly specific SK2 peptide inhibitor (Shakkottai et al, *J. Biol. Chem.* 2001; 276: 43145–43151.). Consistent with the Nernst potential for potassium, the Kv1.3 current was inward between –40 and 0 mV, and outward beyond 0 mV, and was unaffected by Lei-Dab[7] (FIG. 9A). The native SK2 current was suppressed by SKCa3-1b, while the control Kv1.3 current was unaffected (FIG. 9B). This effect was specific since transfection of the GFP vector alone had no effect on either current (FIG. 9C). All experiments were done with symmetric (160 mM) $K^+$ as internal and external recording solutions. The ability of SKCa3-1b to suppress channels composed of SK3 and SK2 subunits, suggests a potent form of negative dominant inhibition that may affect an entire sub-family of $K^+$ channels, a channel family known to play a key role in regulating neuronal electrical firing frequency.

EXAMPLE 13

Sequestration of Native SK3 Via Dominant-Negative Suppression by SKCa3-1B

Figure 10:
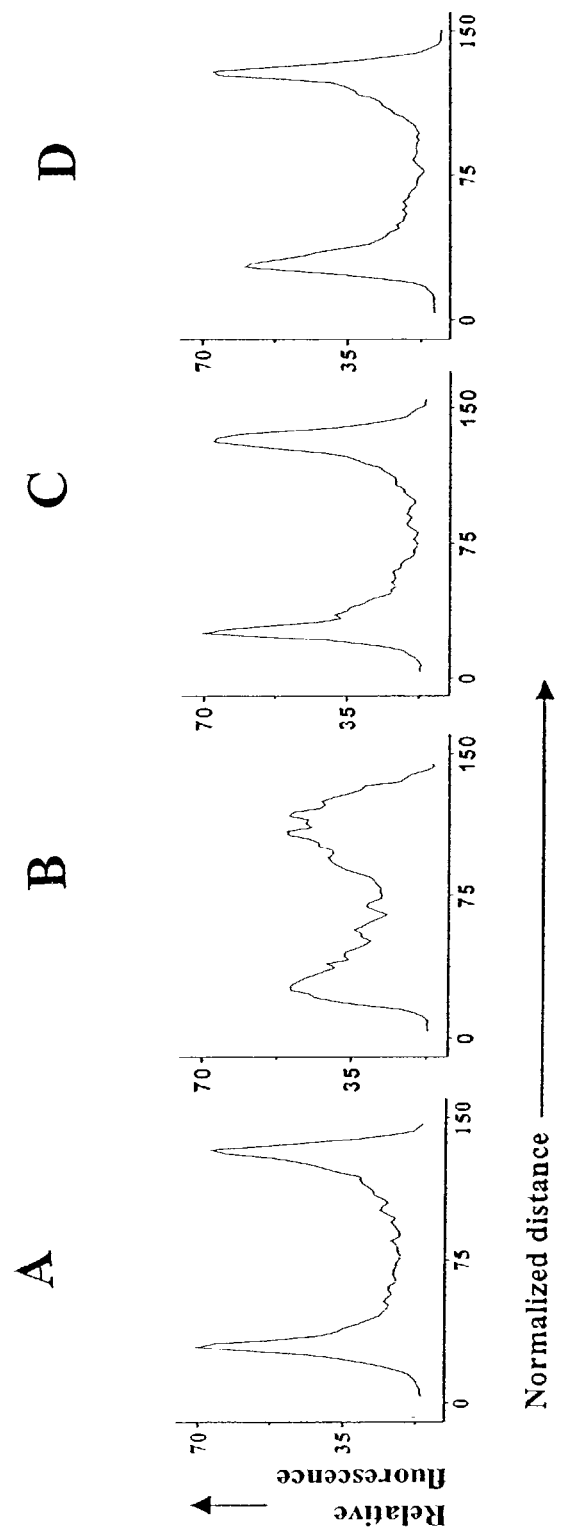
FIG. 10 shows the altered sub-cellular expression pattern of native SK3 in PC12 cells transfected with SKCa3-1b, as set forth in Example 13.

Immunolabeling and confocal microscopy experiments were performed on PC12 cells to discern whether the dominant inhibitory effect of SKCa3-1b was due to its ability to alter the sub-cellular localization of native SK3. Endogenous SK3 protein was identified in this cell with an antibody that reacts only with the N-terminus of the full-length SK3 protein (Wolfart et al, *J. Neurosci.* 2001; 21: 3443–3456.) followed by a fluorescent (Alexa-594 conjugated) red secondary antibody. SK3 staining exhibited an annular pattern consistent with cell membrane expression. Using Scion image software the pixel intensity of presumptive membrane and intracellular SK3 fluorescence was determined, and the average intensity histogram is shown in FIG. 10A.

The sub-cellular localization of endogenous SK3 changed significantly following transfection of SKCa3-1b-GFP. In cells expressing SKCa3-1b-GFP, native SK3 exhibited a red intracellular speckled pattern with diminished fluorescence intensity at the cell periphery. The average intensity histogram of SK3 fluorescence (FIG. 10B) was strikingly different from that of the native channel in untransfected cells. The sharp peaks evident in untransfected PC12 (FIG. 10A) reflect the predominantly annular distribution of the native SK3 channel protein. In contrast, in SKCa3-1b transfected cells, a greater proportion of the native SK3 protein is located intracellularly (FIG. 10B). To control for non-specific effects the same constructs were used that had been used in the electrophysiology studies: GFP vector alone (FIG. 10C) or GFP-tagged Kv1.7 (FIG. 10D). These control constructs were expressed at a higher level (mean pixel intensity: 170–180) than SKCa3-1B (mean pixel intensity: 108). Although GFP- and GFP-Kv1.7 transfected cells showed some degree of intracellular speckling, the pattern was predominantly annular and the average intensity histogram data from multiple cells (FIGS. 10C, 10D) were similar to untransfected cells (FIG. 10A). The ratio of presumptive membrane to intracellular SK3 fluorescence was estimated from the intensity histograms. The ratio in SKCa3-1b-GFP-transfected PC12 cells (1.1±0.09; mean±SEM) was significantly different (p<0.001) from that in untransfected cells (1.72±0.08) or in cells transfected with GFP vector (1.98±0.09) or GFP-Kv1.7 (1.76±0.09). These results taken together with the electrophysiological analysis suggests that SKCa3-1B achieves dominant-negative inhi bition of endogenous SK currents in PC12 and Jurkat cells by decreasing the abundance of functional channels in the plasma membrane, possibly by selectively co-assembling with and sequestering native SK protein in intracellular compartments.

Although the invention has been described with reference to the above examples, it will be understood that modifications and variations are encompassed within the spirit and scope of the invention. Accordingly, the invention is limited only by the following claims.

What is claimed is:

1. An isolated polynucleotide selected from the group consisting of:
   a) SEQ ID NO:2;
   b) SEQ ID NO:2, wherein T can also be U; and
   c) nucleic sequences complementary to SEQ ID NO:2.

2. The polynucleotide of claim 1, wherein the polynucleotide is isolated from a mammalian cell.

3. The polynucleotide of claim 2, wherein the mammalian cell is selected from the group consisting of mouse, rat, and human cell.

4. An expression vector comprising the polynucleotide of claim 1.

5. The vector of claim 4, wherein the vector is a plasmid.

6. The vector of claim 4, wherein the vector is a viral vector.

7. The vector of claim 6, wherein the viral vector is a retroviral vector.

8. An isolated host cell containing the vector of claim 4.

9. The isolated host cell of claim 8, wherein the cell is a prokaryotic cell.

10. The isolated host cell of claim 8, wherein the cell is a eukaryotic cell.

11. The polynucleotide of claim 1, wherein said polynucleotide is operatively linked to an expression control sequence.

12. The polynucleotide of claim 11, wherein the expression control sequence is a promoter.

13. The polynucleotide of claim 12, wherein the promoter is tissue specific.

14. An isolated polynucleotide consisting of SEQ ID NO:2.

* * * * *